United States Patent
Jordan et al.

(10) Patent No.: US 12,350,524 B2
(45) Date of Patent: *Jul. 8, 2025

(54) TREATING DEGENERATIVE DEMENTIA WITH LOW INTENSITY FOCUSED ULTRASOUND PULSATION (LIFUP) DEVICE

(71) Applicant: Brainsonix Corporation, Sherman Oaks, CA (US)

(72) Inventors: Shelly Jordan, Sherman Oaks, CA (US); Mark Evan Schafer, Ambler, PA (US); Alex Korb, Sherman Oaks, CA (US); Walter William Wurster, Sherman Oaks, CA (US)

(73) Assignee: BRAINSONIX CORPORATION, Sherman Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/474,135

(22) Filed: Sep. 25, 2023

(65) Prior Publication Data
US 2024/0278040 A1    Aug. 22, 2024

Related U.S. Application Data

(60) Continuation of application No. 17/193,087, filed on Mar. 5, 2021, now Pat. No. 11,766,576, which is a
(Continued)

(51) Int. Cl.
*A61N 7/00* (2006.01)
*A61B 8/00* (2006.01)
(Continued)

(52) U.S. Cl.
CPC ............... *A61N 7/00* (2013.01); *A61B 8/488* (2013.01); *A61N 7/02* (2013.01); *A61B 8/0808* (2013.01);
(Continued)

(58) Field of Classification Search
CPC .... A61N 7/00; A61N 7/02; A61N 2007/0091; A61B 90/11; A61B 8/4227
See application file for complete search history.

(56) References Cited

U.S. PATENT DOCUMENTS

| 4,343,301 A | 8/1982 | Indech |
| 5,211,160 A | 5/1993 | Talish |

(Continued)

FOREIGN PATENT DOCUMENTS

| EP | 0331348 A1 | 9/1989 |
| EP | 3554636 A1 | 10/2019 |

(Continued)

OTHER PUBLICATIONS

Jordao, JF etal., "Amyloid-beta plaque reduction, endogenous antibody delivery and glial activation by brain-targeted, transcranial focused ultrasound," ExpNeurol. Oct. 2013; 248: 16-29. (Year: 2013).*

(Continued)

*Primary Examiner* — Eric D. Bertram
(74) *Attorney, Agent, or Firm* — Schwabe Williamson & Wyatt

(57) ABSTRACT

Ultrasonic energy is used for treating degenerative dementia. A focal point of an ultrasonic transducer beam is directed at a target area of the brain to promote removal of substances that accumulate in the interstitial pathways that are at least partially responsible for the degenerative dementia. In one example, the target area of the brain may comprise the hippocampus and the degenerative dementia may be Alzheimer's disease. The ultrasonic beam may stimulate brain tissue at a frequency that corresponds to a naturally occurring deep sleep burst frequency of neurons and subsequent astrocyte activation patterns that drive a convective process responsible for brain solute disposal. For example, the transducer may generate a burst frequency of between
(Continued)

Short Pulse Trains Repeated at 1-4Hz 1-4 hertz to stimulate deep sleep brain functions that help remove amyloid plaque.

7 Claims, 20 Drawing Sheets

Related U.S. Application Data continuation of application No. 15/842,771, filed on Dec. 14, 2017, now Pat. No. 10,974,078, which is a continuation-in-part of application No. 15/456,266, filed on Mar. 10, 2017, now Pat. No. 10,792,519, and a continuation-in-part of application No. 15/382,351, filed on Dec. 16, 2016, now Pat. No. 10,512,794, said application No. 15/456,266 is a division of application No. 14/478,323, filed on Sep. 5, 2014, now Pat. No. 9,630,029, which is a division of application No. 13/728,392, filed on Dec. 27, 2012, now Pat. No. 9,061,133.

(60) Provisional application No. 62/434,744, filed on Dec. 15, 2016.

(51) Int. Cl.
*A61N 7/02* (2006.01)
*A61B 8/08* (2006.01)
*A61B 90/11* (2016.01)

(52) U.S. Cl.
CPC ............ *A61B 8/4227* (2013.01); *A61B 90/11* (2016.02); *A61N 2007/0026* (2013.01); *A61N 2007/0091* (2013.01)

(56) References Cited

U.S. PATENT DOCUMENTS

| | | | |
|---|---|---|---|
| 5,247,935 A | 9/1993 | Cline | |
| 5,275,165 A | 1/1994 | Ettinger | |
| 5,282,593 A | 2/1994 | Fast | |
| 5,291,890 A | 3/1994 | Cline | |
| 5,323,779 A | 6/1994 | Hardy | |
| 5,381,794 A | 1/1995 | Tei | |
| 5,409,446 A | 4/1995 | Rattner | |
| 5,546,438 A | 8/1996 | Hynecek | |
| 5,738,625 A | 4/1998 | Gluck | |
| 5,752,515 A | 5/1998 | Jolesz | |
| 6,066,123 A | 5/2000 | Li | |
| 6,088,613 A | 7/2000 | Unger | |
| 6,094,598 A | 7/2000 | Elsberry | |
| 6,148,225 A | 11/2000 | Kestler | |
| 6,198,956 B1 | 3/2001 | Dunne | |
| 6,198,958 B1 | 3/2001 | Ives | |
| 6,261,231 B1 | 7/2001 | Damphousse | |
| 6,267,734 B1 | 7/2001 | Ishibashi | |
| 6,348,793 B1 | 2/2002 | Balloni | |
| 6,413,216 B1 | 7/2002 | Cain | |
| 6,612,988 B2 | 9/2003 | Maor | |
| 6,708,051 B1 | 3/2004 | Durousseau | |
| 7,283,861 B2 | 10/2007 | Bystritsky | |
| 7,300,414 B1 | 11/2007 | Holland | |
| 7,427,265 B1 | 9/2008 | Keilman | |
| 7,450,985 B2 | 11/2008 | Meloy | |
| 7,505,807 B1 | 3/2009 | Kucharczyk | |
| 7,896,821 B1* | 3/2011 | Magnin | A61M 37/0092 |
| | | | 601/2 |
| 8,086,296 B2 | 12/2011 | Bystritsky | |
| 8,343,083 B1 | 1/2013 | Fencel | |
| 9,061,133 B2* | 6/2015 | Wurster | A61B 8/4227 |
| 9,630,029 B2* | 4/2017 | Wurster | A61B 8/4227 |
| 10,265,497 B2 | 4/2019 | Tsai | |
| 10,512,794 B2* | 12/2019 | Wurster | A61B 90/10 |
| 10,792,519 B2* | 10/2020 | Wurster | A61N 7/02 |
| 10,974,078 B2* | 4/2021 | Jordan | A61N 7/02 |
| 11,311,748 B2* | 4/2022 | Wurster | A61N 7/00 |
| 11,766,576 B2* | 9/2023 | Jordan | A61N 7/02 |
| | | | 601/2 |
| 2002/0042121 A1 | 4/2002 | Riesner | |
| 2002/0103436 A1 | 8/2002 | Njenanze | |
| 2002/0127230 A1 | 9/2002 | Chen | |
| 2002/0173697 A1 | 11/2002 | Lenhardt | |
| 2003/0204135 A1 | 10/2003 | Bystritsky | |
| 2004/0048795 A1 | 3/2004 | Ivanova | |
| 2005/0020945 A1 | 1/2005 | Tosaya | |
| 2005/0240126 A1 | 10/2005 | Roley | |
| 2006/0184069 A1 | 8/2006 | Vaitekunas | |
| 2006/0191926 A1 | 8/2006 | Ray | |
| 2007/0016031 A1 | 1/2007 | Mourad | |
| 2007/0299370 A1 | 12/2007 | Bystritsky | |
| 2008/0262350 A1 | 10/2008 | Unger | |
| 2008/0275340 A1 | 11/2008 | Beach | |
| 2009/0005711 A1 | 1/2009 | Konofagou | |
| 2009/0112133 A1 | 4/2009 | Deisseroth | |
| 2009/0254154 A1 | 10/2009 | De Taboada | |
| 2010/0010394 A1 | 1/2010 | Liu | |
| 2010/0123529 A1 | 5/2010 | Chang | |
| 2011/0092800 A1 | 4/2011 | Yoo | |
| 2011/0094288 A1 | 4/2011 | Medan | |
| 2011/0166444 A1 | 7/2011 | Elgort | |
| 2011/0172653 A1 | 7/2011 | Schneider | |
| 2011/0213200 A1 | 9/2011 | Mishelevich | |
| 2011/0264012 A1 | 10/2011 | Lautzenhiser | |
| 2012/0060847 A1 | 3/2012 | Stratton | |
| 2012/0083719 A1 | 4/2012 | Mishelevich | |
| 2012/0197166 A1 | 8/2012 | Gertner | |
| 2012/0296241 A1 | 11/2012 | Mishelevich | |
| 2014/0058293 A1 | 2/2014 | Hynynen | |
| 2014/0074181 A1 | 3/2014 | Slutsky | |
| 2014/0186423 A1 | 7/2014 | Gelfand | |
| 2014/0188011 A1 | 7/2014 | Wurster | |
| 2014/0343463 A1* | 11/2014 | Mishelevich | A61N 7/00 |
| | | | 601/2 |
| 2015/0025421 A1* | 1/2015 | Wagner | A61N 1/0408 |
| | | | 607/45 |
| 2015/0283392 A1 | 10/2015 | Bourke, Jr. | |
| 2015/0297176 A1 | 10/2015 | Rincker | |
| 2016/0001096 A1* | 1/2016 | Mishelevich | A61B 90/37 |
| | | | 601/2 |
| 2016/0067526 A1 | 3/2016 | Yang | |
| 2017/0105700 A1 | 4/2017 | Bar-Zion | |
| 2017/0182339 A1 | 6/2017 | Wurster | |
| 2018/0117364 A1 | 5/2018 | Jordan | |
| 2018/0304101 A1* | 10/2018 | Yang | A61N 7/00 |
| 2019/0021666 A1 | 1/2019 | Nyhynen | |
| 2019/0142513 A1 | 5/2019 | Witte | |
| 2020/0121958 A1 | 4/2020 | Wurster | |
| 2020/0123681 A1 | 9/2020 | Zuk | |
| 2022/0054853 A1 | 2/2022 | Bystritsky | |

FOREIGN PATENT DOCUMENTS

| | | |
|---|---|---|
| JP | 2020-501734 | 1/2020 |
| JP | 2022-62218 | 4/2022 |
| WO | 2017/195309 A1 | 11/2017 |
| WO | 2018/112269 A1 | 6/2018 |
| WO | 2021/236455 A1 | 11/2021 |
| WO | 2022/046764 A1 | 3/2022 |

OTHER PUBLICATIONS

Leinenga, G., et al. "Scanning ultrasound removed amyloid-beta and restore smemory in an Alzheimer's disease mouse model," Scie Trans IMed.; Mar. 11, 2015; 7 (278). (Year: 2015).*

Yoo, et al., Focused ultrasound modulates region-specific brain activity, Elsevier Journal—NeuroImage, vol. 56, 2011, pp. 1267-1275.

Mulgaonkar et al., A prototype stimulator system for noninvasive low intensity focused ultrasound delivery; Stud Health Technol Inform, vol. 173, 2012, pp. 297-303.

(56) References Cited

OTHER PUBLICATIONS

Min et al., Focused ultrasound-mediated suppression of chemically-induced acute epileptic EEG activity, BMC Neuroscience; 2011, 12:23, pp. 1-12.
Bystritsky et al., "A review of low-intensity focused ultrasound pulsation", Elsevier Journal—Brain Stimulation, vol. 4, 2011, pp. 125-136.
Barlow, et al., The risk of seizure after receipt of whole-cell pertussis or measles, mumps, and rubella vaccine, New England journal of Medicine, vol. 345, No. 9, pp. 656-661 (2001).
Tyler, et al., Remote excitation of neuronal circuits using low-intensity, low-frequency ultrasound, PlosOne, vol. 3, Issue 10, pp. 1-11 (Oct. 2008).
Turfail, et al., Ultrasonic neuromodulation by brain stimulation with transcranial ultrasound, Nature Protocols, vol. 6, No. 9, pp. 1453-1470 (2011).
Clement et al., A hemisphere array for non-invasive brain therapy and surgery, Physics in Medicine and Biology, vol. 45, No. 12, pp. 3707-3719 (2000).
Colucci et al., Focused ultrasound effects on nerve action potential in vitro, Ultrasound in Med. & Biol., vol. 35, No. 10, pp. 1737-1747 (2009).
Tufail, et al., Transcranial Pulsed Ultrasound Stimulates Intact Brain Circuits, Neuron, vol. 66, pp. 681-694 (Jun. 10, 2010).
Yang, et al., Transcranial focused ultrasound to the thalamus is associated with reduced extracellular GABA levels in rats, Neuropsychobiology, vol. 65, pp. 153-160 (2012).
Yoo, et al., Transcranial focused ultrasound to the thalamus alters anesthesia time in rats, Neuroreport, vol. 22(15), pp. 783-787 (Oct. 26, 2011).
Hameroff, et al., Transcranial ultrasound (TUS) effects on mental states: a pilot study, Brain Stimulation, vol. 6, pp. 409-415 (2013).
Korb, et al., Low-intensity focused ultrasound pulsation device used during magnetic resonance imaging: evaluation of magnetic resonance imaging-related heating at 3 Tesla/128MHz, Neuromodulation, (2013).
Bystritsky et al., A preliminary study of fMRI-guided rTMS in the treatment of generalized anxiety disorder, J Clin Psychiatry, vol. 69, pp. 1092-1098 (Jul. 7, 2008).
Deffieux et al., Low-intensity focused ultrasound modulates monkey visuomotor behavior, Current Biology, vol. 23, pp. 2430-2433 (Dec. 2, 2013).
Mehic et al., Increased anatomical specificity of neuromodulation via modulated focused ultrasound, Plos One, vol. 9, Issue 2, pp. 1-13 (Feb. 2014).
Kim et al., Estimation of the spatial profile of neuromodulaton and the temporal latency in motor responses induced by focused ultrasound brain stimulation, Neurophysiology Neuroreport, vol. 25, No. 7., pp. 475-479 (2014).
Metwally, et al., Influence of the antisotropic mechanical properties of the skull in low-intensity focused ultrasound towards neuromodulation of the brain, 35th Ann Int Conf of IEEE EMBS, Osaka, Japan pp. 4565-4568 (Jul. 3-7, 2013).
Winhye, et al., Creation on various skin sensations using pulsed focused ultrasound: evidence for functional neuromodulation, International Journal of Imaging Systems and Technology, (Dec. 27, 2013).
Tyler et al., Remote excitation of neuronal circuits using low intensity, low frequency ultrasound, Ultrasonic Neurostimulation, vol. 3, No. 10, pp. 1-11 (2008).
Tyler, W.J., Noninvasive Neuromodulation with Ultrasound? A continuum mechanics hypothesis, pp. 1-12 (2010).
Jordao, JF et al., "Amyloid-beta plaque reduction, endogenous antibody delivery and glial activation by brain-targeted, transcranial focused ultrasound," Exp Neurol. Oct. 2013; 248: 16-29. Published online May 21, 2013; retrieved from the Internet <https://www.sciencedirect.com/science/article/pll/S0014488613001544?via%3Dihub> <doi: 10.1016/j.expneurol.2013.5.008>.
Leinenga, G., et al. "Scanning ultrasound removed amyloid-beta and restores memory in an Alzheimer's disease mouse model," Scie Transl Med.; Mar. 11, 2015; 7 (278):278ra33. Retrieved from the Internet <http://stm.sciencemag.org/content/7/278/278ra33> <doi: 10.1126/scitranslmed.aaa2512>.
International Search Report and Written Opinion for PCT/SU2021/047344 dated Nov. 30, 2021; 15 pages.
Ghodgaonkar et al., "Microwave Nondestructive Testing of Composite Materials using Free-Space Microwave Measurement Techniques" Oct. 21, 2000 [retrieved on Nov. 3, 2021] <https://www.ndt.net/article/wcndt00/papers/idn251/idn251.htm> entire document.
Selbekk et al., "Ultrasound imaging in neurosurgery: approaches to minimize surgically induced image artefacts for improved resection control" Mar. 5, 2013 [retrieved on Nov. 3, 2021] Retrieved from the Internet <URL: https://link.springer.com/content/pdf/10.1007/s00701-013-1647-7.pdf> entire document.
He, et al., "Overexpression of Slit2 decreases neuronal excitotoxicity accelerates glymphatic clearance, and improves cognition in a multiple microinfarcts model", Aug. 10, 2020; retrieved from the Internet <https://assets.researchsquare.com/files/rs-32713/v2/0bea5b9c-b353-4016-b41c-9640550faae7.pdf?c=1631850797>.

* cited by examiner

Short Pulse Trains Repeated at 1-4Hz

TREATING DEGENERATIVE DEMENTIA WITH LOW INTENSITY FOCUSED ULTRASOUND PULSATION (LIFUP) DEVICE

CROSS-REFERENCE TO RELATED APPLICATIONS

The present application is a continuation of U.S. patent application Ser. No. 17/193,087, filed Mar. 5, 2021, now U.S. Pat. No. 11,766,576, issued Sep. 26, 2023, which is a continuation of U.S. patent application Ser. No. 15/842,771 ("the '771 application"), filed Dec. 14, 2017, issued as U.S. Pat. No. 10,974,078, which is hereby incorporated by reference in its entirety. The '771 application claims priority to Provisional Patent Application, Ser. No. 62/434,744 filed Dec. 15, 2016, entitled TREATING DEGENERATIVE DEMENTIA USING LOW INTENSITY FOCUSED ULTRASOUND PULSATION (LIFUP) DEVICE, which is hereby incorporated by reference in its entirety. The '771 application is a continuation-in-part of U.S. patent application Ser. No. 15/382,351 filed Dec. 16, 2016, issued as U.S. Pat. No. 10,512,794, entitled STEREOTACTIC FRAME, which is hereby incorporated by reference in its entirety. The '771 application is also a continuation-in-part of U.S. patent application Ser. No. 15/456,266, filed Mar. 10, 2017, issued as U.S. Patent No. 10,792,519, entitled FOCUSED ULTRASONIC TRANSDUCER NAVIGATION SYSTEM, which is a divisional patent application of U.S. patent application Ser. No. 14/478,323, filed on Sep. 5, 2014, issued as U.S. Pat. No. 9,630,029, entitled FOCUSED ULTRASONIC TRANSDUCER NAVIGATION SYSTEM, which is a divisional patent application of U.S. patent application Ser. No. 13/728,392, filed Dec. 27, 2012, issued as U.S. Pat. No. 9,061,133, all of which are hereby incorporated by reference in their entireties.

COPYRIGHT NOTICE

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

TECHNICAL FIELD

The technology relates to treating degenerative dementia using low intensity focused ultrasound pulsation (LIFUP).

BACKGROUND

Ultrasonic energy is used to treat different medical conditions. During treatment, transducers apply ultrasonic energy to a treatment zone or "target" within a patient. For example, the ultrasonic energy may be applied to a clot to dissolve or remove a blockage within the brain. Of course other types of disorders also may be treated with ultrasonic energy. For example, ultrasonic therapy may be used for treating other psychiatric, neurological, and medical disorders.

Ultrasonic therapy may apply ultrasonic energy to the same treatment zone over multiple treatment sessions. Each treatment session may need to apply the ultrasonic accurately and repeatedly to the same treatment zone. A Magnetic Resonance Imaging (MRI) machine may first scan the brain, or other body part, to locate the target area. The ultrasonic system is then adjusted to focus the ultrasonic energy onto the located target area. Ultrasonic therapy may be time consuming and expensive since each session requires a trip to a hospital and use of a MRI machine to relocate the same target area.

DETAILED DESCRIPTION

Figure 1A:
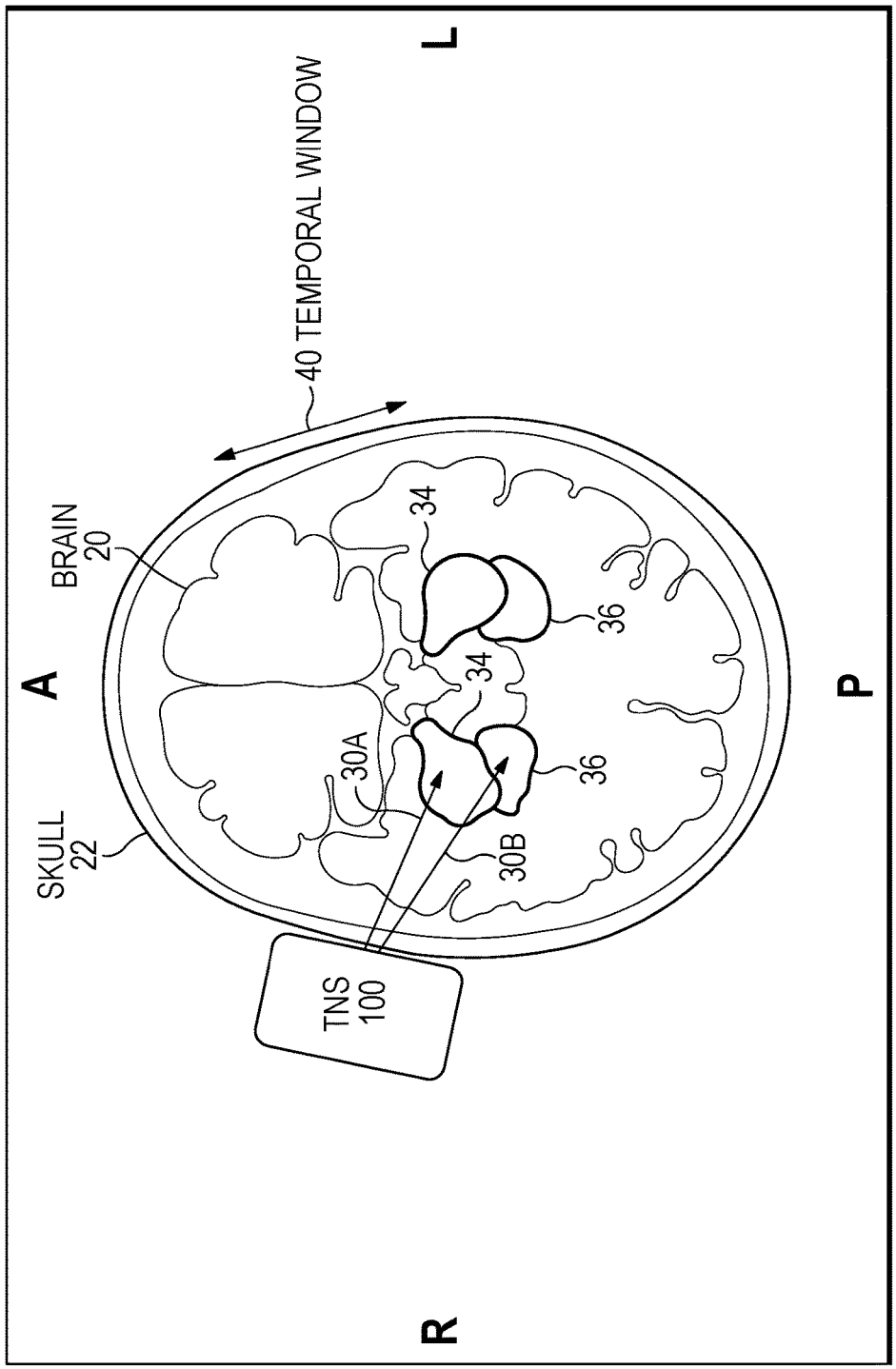
FIG. 1A is a focused ultrasonic transducer navigation system used for treating degenerative dementia.

A transducer system uses low intensity focused ultrasound pulsation (LIFUP) in a unique way to remove substances that may accumulate in the interstitial spaces of the brain that are believed to be at least partially responsible for degenerative dementia, including Alzheimer's disease, Parkinson's dementia, frontal lobe dementia, and other degenerative processes.

One symptom of degenerative dementia is a lack of deep sleep. Deep sleep may promote the removal of toxic byproducts that develop in the interstitial spaces of the brain during awake states. During deep sleep, the interstitial spaces may open up. Astrocyte cells within the brain include fingers that may produce a convective force that moves fluid along the interstitial spaces flushing out amyloid precursor proteins that may turn into plaque if not swept out.

The finger like astrocyte projections providing the plaque removing convection forces appear to be excited by neurons that activate at a rate of around once per second. In other words, electrical waves of around 1-4 cycles per second produced by the brain during deep sleep may stimulate the astrocyte cell fingers and help prevent amyloid plaque buildup that contributes to degenerative dementia.

The transducer system may generate ultrasonic waves at the same 1-4 Hertz cycles normally produced during deep sleep helping to open up interstitial spaces and stimulate the astrocyte cells that may flush dementia causing amyloid plaque from the brain.

The present ultrasound device and procedure uses focused and pulsatile ultrasound that targets and optimally stimulates brain tissue at a frequency that corresponds to the naturally occurring burst frequency of neurons and subsequent astrocyte activation patterns that appear to drive the convective process responsible for brain solute disposal. The ultrasonic treatment may be applied during natural or sedated sleep to optimize solute removal with sonolysis caused by the interstitial spaces opening and improved glymphatic flow during sleep.

An ultrasonic probe is initially targeted using anatomical MRI images and optionally with co-registered functional images with brain site aiming based on an individual's surface fiducials which have been correlated with imaging surface landmarks. Scalp location and angulation settings for the probe use standard surface measurement techniques as in standard electroencephalogram (EEG) placement techniques or optionally using MRI based optical tracking equipment. While in an MRI scanner, targeting is confirmed using Arterial spin labeling activation patterns or optionally another blood oxygen level dependent (BOLD) protocol.

The ultrasonic therapy may be applied during a patient sleep state for optimum opening up of the interstitial spaces of the brain. In one example, sedation is obtained using dexmedetomidine or other agents designed to block norepinephrine. Blocking norepinephrine innervation may shrink astrocytes which further open the interstitial pathways.

In one example, the pulse frequency will be at 1-4 Hertz to correspond with the naturally occurring predominant brain rhythms of the sleep state. Maximum power settings will be utilized as set forth by Food and Drug Administration (FDA) regulations. One example therapy may include 30-90 minute treatments twice per week and may continue until the patient demonstrates stabilization or improvement of repeatable cognitive measures including, but not limited to, resting brain networks (RBNS) and Montreal cognitive assessment (MOCA). Plaque removal can be followed with position emission tomography (PET) scans and lumbar puncture cerebral spinal fluid (CSF) sampling.

Site targeting within the brain may depend on which cognitive domain is most affected for each patient. For example, the hippocampus through a temporal scalp window may be targeted for Alzheimer's disease with predominant amnestic syndrome which primary affects the hippocampus. The transducer system may target other areas of the brain for other degenerative dementias. For example, the transducer system may focus ultrasonic waves at a different area of the temporal lobe associated with language functions. In one example, a patient may show signs of both memory and language loss and ultrasonic waves may be applied to both associated areas of the brain.

Transcranial Ultrasound Treatment of Degenerative Dementia

FIG. 1A shows a transducer navigation system (TNS) 100 used for treating degenerative dementia, such as Alzheimer's disease and other neurodegenerative conditions characterized by extracellular deposits of material which are apparently toxic and which may accelerate additional deposit accretion by obstructing the flushing effects of interstitial flow.

Figure 1B:
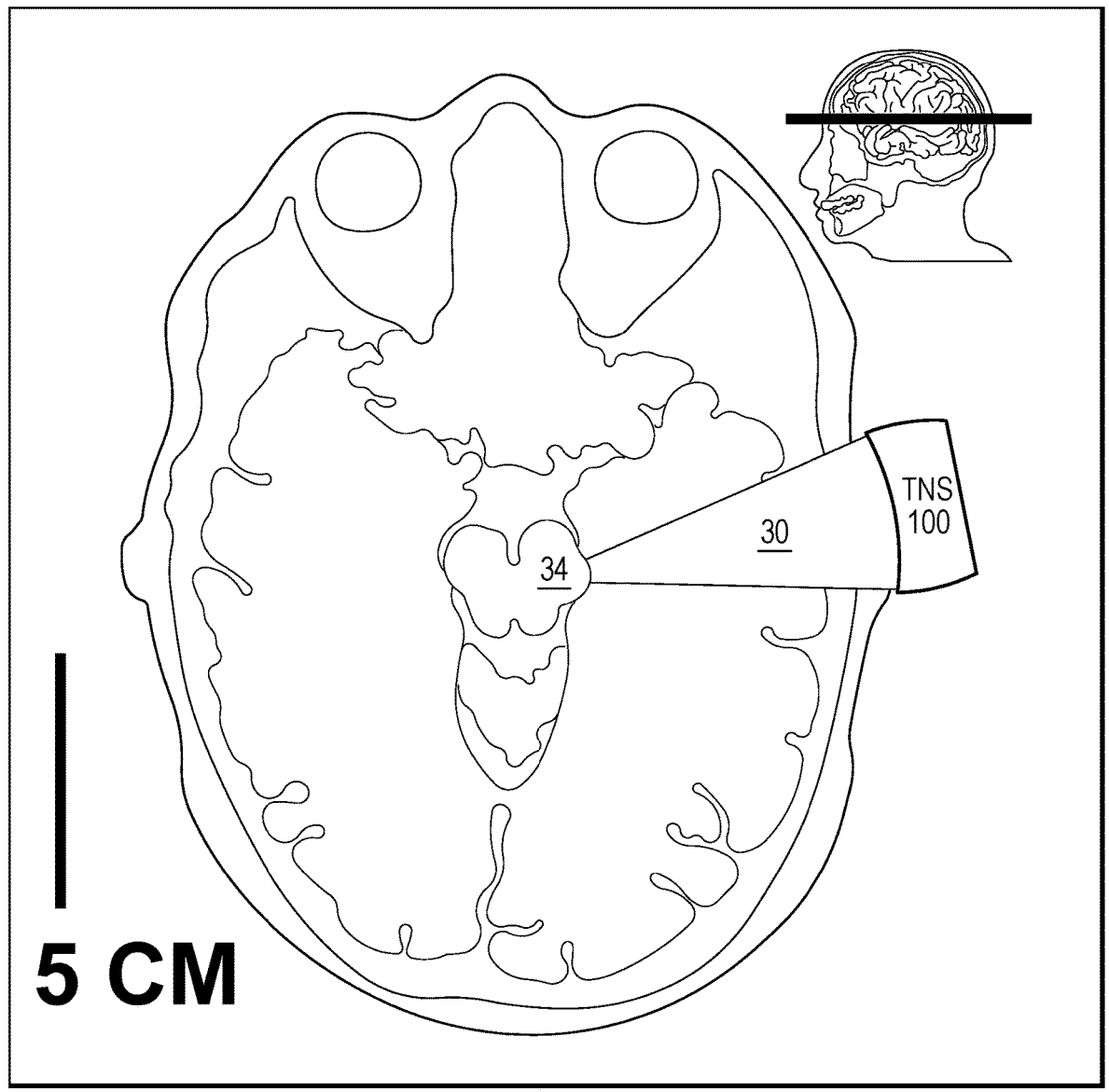
FIG. 1B shows the transducer system targeted at the hippocampal formation and entorhinal cortex.

FIG. 1B shows an axial section through the mesial temporal lobe and TNS 100 targeted at the hippocampal formation and entorhinal cortex 34. Targets 34 are deep below the temporal ultrasound window in the 3.5 to 5 cm range from the surface. TNS 100 may focus ultrasonic waves 30 on target 34 for patients with Alzheimer's disease or other degenerative conditions with predominant memory loss symptoms (amnestic syndrome). These cases are characterized by amyloid deposits that disrupt the mesial temporal structures.

Figure 1C:
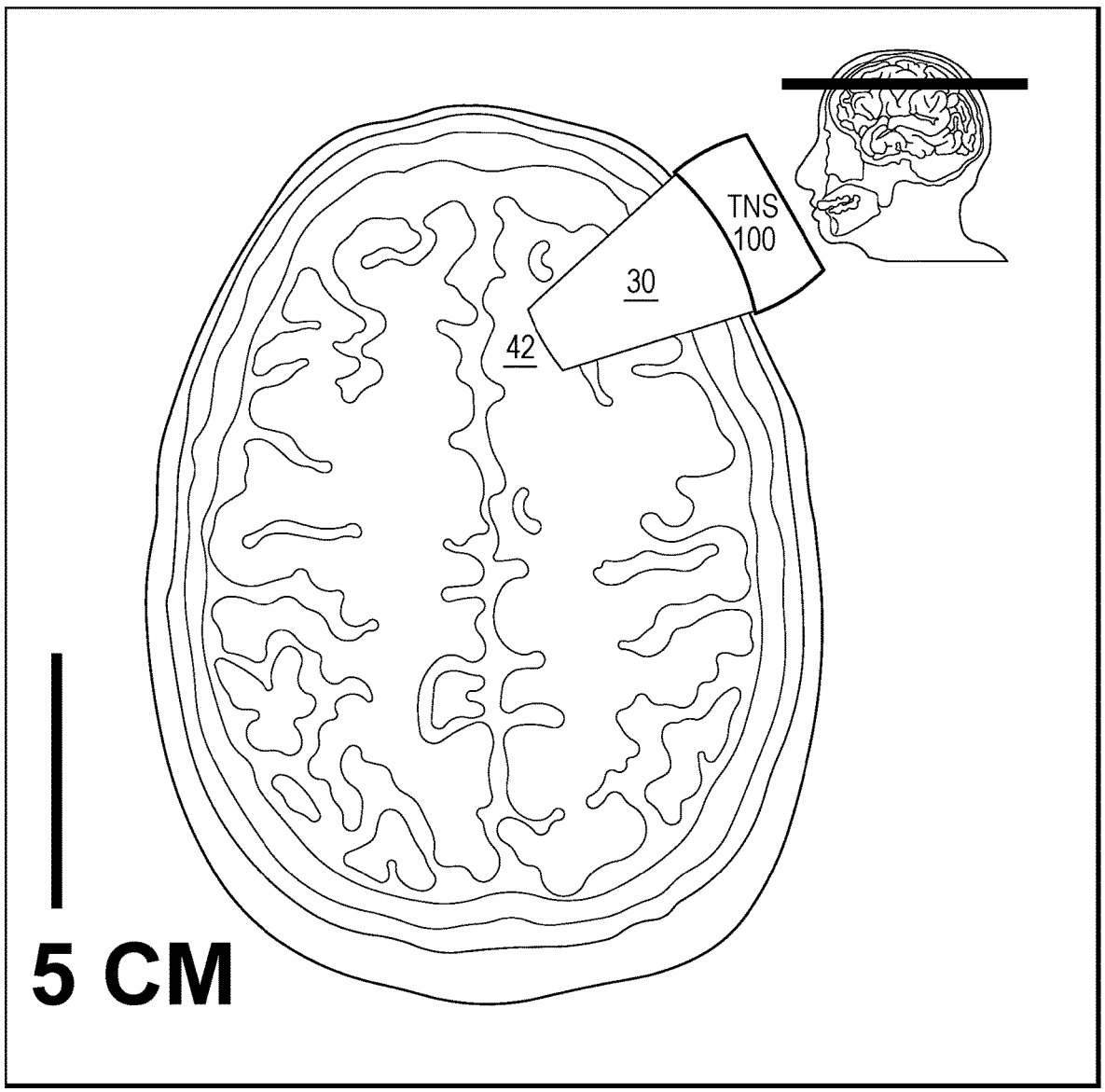
FIG. 1C shows the transducer system targeted at a prefrontal brain region.

FIG. 1C shows an axial section through a prefrontal region 42. Targets 42 are shallower than in FIGS. 1A and 1B. Brodmann areas 46 and 9 appear to be associated with executive function. TNS 100 may focus ultrasound waves 30 at prefrontal targets in the 2.5 to 3.5 cm range for patients with dysfunction predominantly affecting target area 42.

Figure 1D:
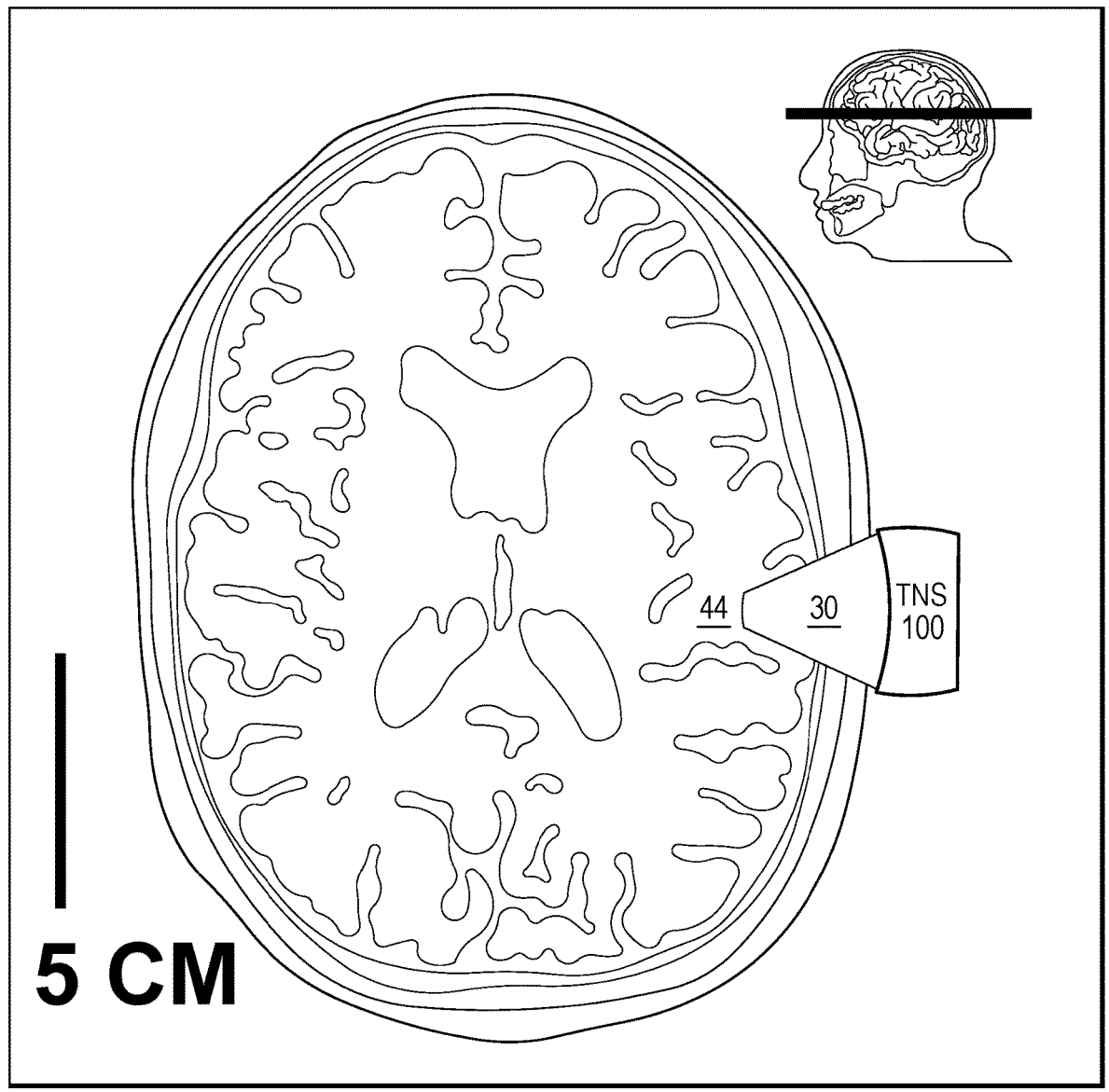
FIG. 1D shows the transducer system targeted at a parietal temporal junction.

FIG. 1D shows an axial section through a parietal temporal junction area associated with patients with language disturbance associated with Alzheimer's disease (logopenic syndrome). TNS 100 may focus ultrasonic waves 30 at target area 44 in the 2.5 to 3.5 cm range. Apraxic speech localization is more anterior in the frontal operculum. Likewise, more rostral and anterior localizations are used for patients with Parkinson's that have predominant movement disorders including freezing and motor fluctuations (Brodmann area 6).

The description below may refer to treating Alzheimer's disease. However, it should be understood that the system and methods described below may be used for treating any type of degenerative dementia or any other disease associated with amyloid plaque.

As mentioned above, a significant amount of extracellular waste resulting from brain activity appears to be removed by convection through extracellular spaces extending along perivascular spaces into the cerebrospinal fluid (CSF) space and outwards along lymphatic channels. Numerous trials of agents designed for blocking the production of amyloid plaque with enzymatic inhibitors or accelerating its destruction with antibodies have been unfruitful so far in reversing cognitive impairment although there has been modest slowing of cognitive decline. The failure has been partly attributed to the potential inability to break up the amyloid deposits with enough safety and precision using systemic treatments.

TNS 100 uses a targeted approach for Alzheimer's disease using transcranial ultrasound. Optimal application of sonolysis leverages certain aspects of brain physiology and the pathophysiology of brain fluid dynamics relating to Alzheimer's disease. One factor leveraged includes the known lack of slow wave sleep in Alzheimer's patients and how the inability to attain slow wave sleep constricts the flow of interstitial fluid.

Ultrasonic waves 30 applied by TNS 100 to target areas of brain 20 may foster or simulate slow wave sleep physiology on demand and may reopen pathways for the reestablishment of interstitial fluid convection. TNS 100 optimizes the delivery of ultrasonic energy 30 in a safe and targeted fashion in order to directly break up plaque or to stimulate cellular elements in order to accentuate convective effects in regional areas of interest such as the hippocampus 34, parahippocampal gyrus 36, and other target areas 42 and 44 shown in FIGS. 1C and 1D, respectively.

Slow wave sleep is characterized by one to four Hertz slow waves with scalp EEG recordings and is a state of little observable muscle activity and a reduced ability to arouse. Microelectrode recordings demonstrate bursts of high frequency neuronal firing interspersed with quiet periods recurring at a frequency of one Hertz.

The neuronal bursts release glutamate which induces movements in astrocyte filopodia. The later may contribute on some level to convection forces or shaping the interstitial spaces. EEG surface waves occur in a coherent fashion with a phase lag from frontal to occipital lobe under some conditions but with selective stimulation the day before sleep recordings, the waves can be made to emanate from the site of stimulation outwards. In other words, the wave initiation site reflects targeted stimulation the day before.

If slow waves have a purpose, this functional relationship may be explained by one of two considerations. Either the slow wave initiation reflects a process which is related to memory consolidation, a process that experimentally has been related to slow wave sleep, or, the slow wave initiation site is related to increased need to dispose of activity induced toxic byproducts that would otherwise interfere with learning consolidation.

The latter explanation seems possible since there is a known relationship between lack of slow wave sleep in Alzheimer's disease which is characterized by deposits of amyloid that appear to result from processing of amyloid precursor protein (APP) which is stimulated by synaptic activation.

In deep sleep, the locus coeruleus is relatively inactive. The consequential reduction in norepinephrine input to astrocytes may lead to cell shrinkage and resultant opening of interstitial spaces that should promote convective effects. Notably, locus coeruleus degeneration is a very early event in Alzheimer's disease. However, levels of cerebral norepinephrine, transporter function and receptor densities may be maintained or increased so that any direct potential effect of locus coeruleus neuronal loss is uncertain.

Perhaps of greater significance is the loss of lateral hypothalamic neurons in Alzheimer's disease that are used for triggering deep sleep. The direct effects of not triggering deep sleep and the indirect effects of consequential failure to inhibit residual locus coeruleus function may prevent the coordinated astrocyte morphing required for facilitating interstitial convection.

Correcting conditions that interfere with deep sleep such as sleep apnea and adopting treatment regimens that promote healthier sleep architecture would be strategically sound. How to promote deep sleep on demand may require certain medications. Acutely, anesthetic agents do not simulate normal sleep closely; however, a sedated state characterized by slow waves, along with inhibition of norepinephrine, can be created with short acting agents such as dexmedetomidine.

Prior to applying ultrasonic energy 30 to brain 20, the interstitial spaces are opened up as in slow wave sleep with a norepinephrine blocker such as dexmedetomidine. Then targeted ultrasonic waves 30 are applied to brain 20 to facilitate plaque removal in patients with degenerative dementia, including Alzheimer's disease.

Although there has been some concern about anesthesia as a potential risk factor for dementia, dexmedetomidine has a good safety profile when used in elderly and acutely ill patients. Alternatively, sleep deprivation or withdrawal from armodafinil or other stimulants may be used to induce sleep during ultrasonic wave therapy. The above sleep condition may cause the interstitial pathways to sufficiently open to allow for egress of extracellular waste including amyloid plaque.

Ultrasonic energy 30 from TNS 100 solubilizes, mobilizes and potentially facilitates convective forces. Immune therapy aimed at plaque has been ineffective or minimally effective in promoting an effective dissolution process although there is evidence of partial plaque dissolution and mobilization based on increased levels of amyloid related protein ABeta 42 found in post treatment CSF and peripheral blood samples.

TNS 100 treats amyloid plaque by causing the deformation of acoustic waves by the skull as well as accurately targeting tissue at risk for Alzheimer's disease. For example, TNS 100 can be used for human clot lysis and targeting the hippocampus 34, parahippocampal gyrus 36, and mesial temporal lobe which are the commonly affected structures in patients with Alzheimer's disease.

To prevent skull 22 from impeding ultrasound waves 30, TNS 100 may use a temporal window 40 (FIG. 1A) which is a thin region of the skull that usually allows for successful insonation. However, TNS 100 may be attached to any location on skull 22, such as on the middle of the forehead for target areas in thedorsolateral prefrontal cortex.

Ultrasonic targeting by TNS 100 also may use Doppler imaging from commercially available units to identify the posterior cerebral artery that fortuitously runs just medial to the hippocampal formation 36 and then clamping TNS 100 in a targeted position as described below.

TNS 100 may use other types of advanced targeting and greater target selection that combines multiple ultrasound sources in a spherical array and uses acoustic wave correction for skull distortion and thermal imaging with MRI for high intensity focused ultrasound.

TNS 100 may include a stereotactic head holder device so treatment sessions may proceed outside of the MRI scanner once initial targeting has been performed. Hybrid systems may use multiple detectors through the temporal window without the use of a spherical array.

Mechanical and heating effects may be applied for direct dissolution and mobilization of amyloid plaque. However, the ability of transcranial ultrasound to stimulate neuronal discharge may facilitate convective forces by the release of glutamate and the subsequent activation of astrocyte filopodia. With the latter in mind, TNS 100 may use 1-4 Hertz pulse rates in order to be coherent with natural burst rates of neurons during slow wave sleep.

Simulating Deep Sleep with Ultrasonic Pulsing

Figure 1E:
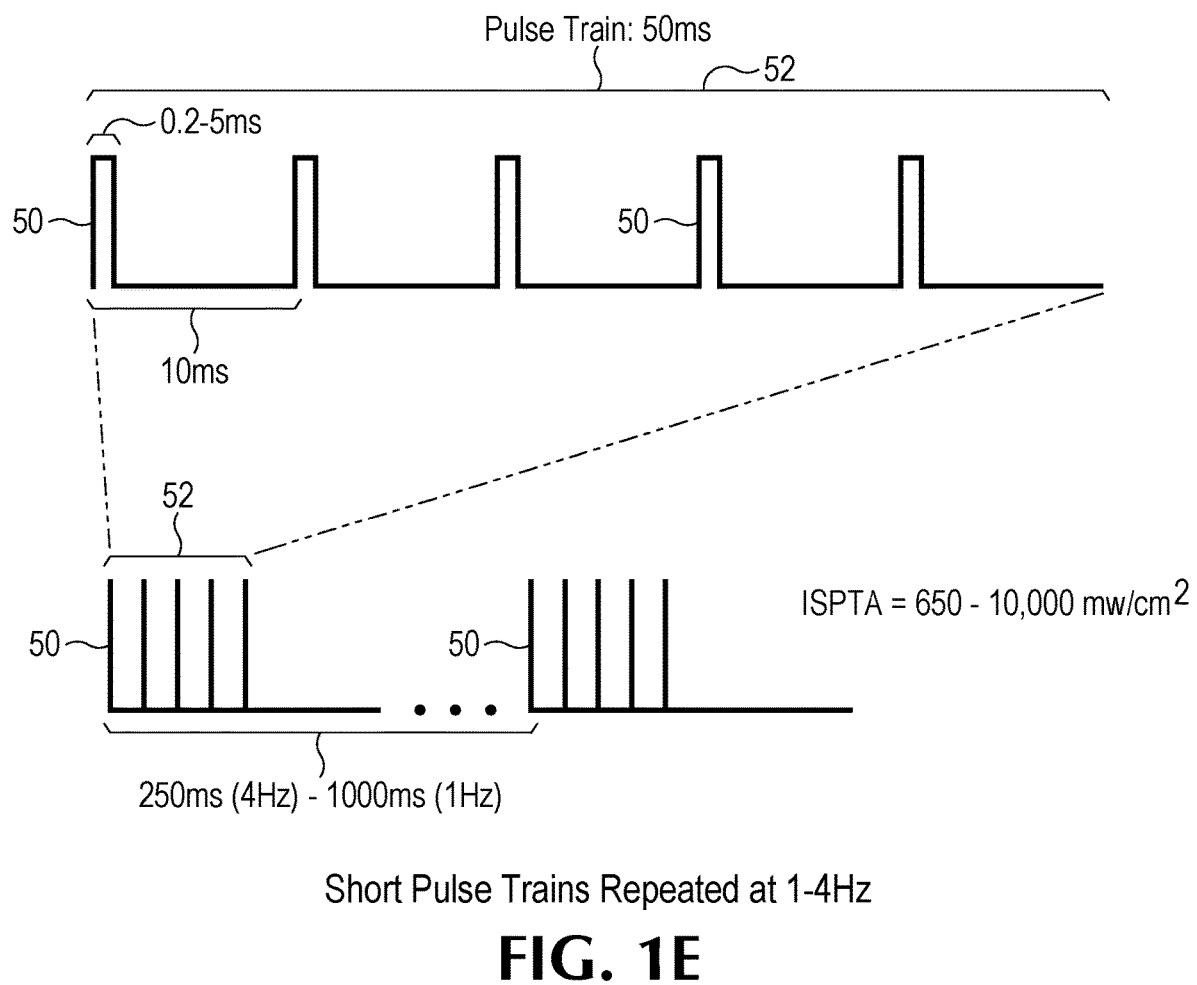
FIGS. 1E and 1F show example pulse waves used by the transducer system for treating degenerative dementia.
Figure 1F:
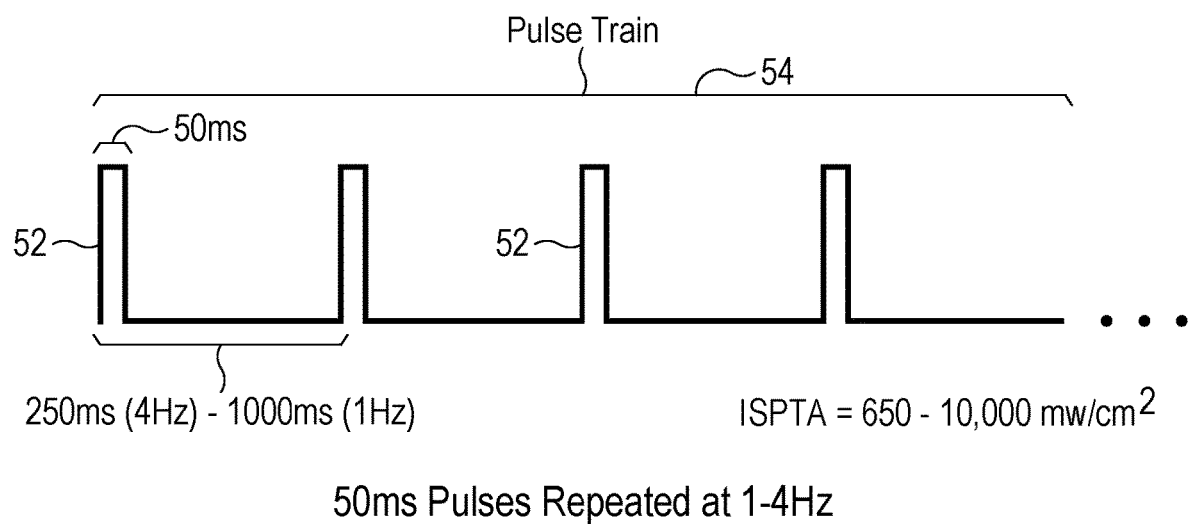

FIGS. 1E and 1F show example ultrasonic pulses generated by TNS 100. As explained above, TNS 100 may generate ultrasonic pulses 50 at a rate or around 1-4 Hertz to simulate deep sleep brain functions that may help remove amyloid plaque. For example, the period of pulses 50 may help open up interstitial spaces in the brain causing astrocyte cell fingers to produce convective forces that help breakup and remove amyloid plaque. The heat produced by pulses 50 on the target areas then further break up the amyloid plaque that is then removed by the astrocyte cell fingers.

In one example, pulse trains 54 are generated at 1-4 Hertz (1000 milliseconds (ms)-250 ms). Pulse trains 54 may include separate groups 52 of pulses 50, such as a series of 5 pulses 50 with a duration of 0.2-5 milliseconds (ms), a period of 10 ms, and a combined duration of 50 ms. Other pulse trains 54 may use more or fewer groups 52 of pulses 50 at longer or shorter durations and periods. For example, pulse train 54 may include single pulses 50 each with a duration of 50 ms and a period of 1-4 Hertz. Pulses 50 represent an on state of TNS 100. During the on state, the transducer in TNS 100 may generate any combination of sinusoidal ultrasonic waves know in the art.

The duration and number of pulses 50 may vary depending on the type of transducer and ultrasonic power output by the transducer. For example, a larger diameter transducer may create a more conical ultrasonic beam that produces higher temperatures. Ultrasonic waves 30 are pulsated to create a temporary rise in brain temperature at the target location without creating lesions, thermal ablation of neural tissue, or any other permanent change in brain structure. Longer duration pulses 50 may create more thermal deposition. The 10 ms period in pulse groups 52 allow brain tissue to rest between each individual pulse 50 while the 1-4 Hz period between pulse groups 52 stimulate deep sleep brain functions, such as the opening up of interstitial spaces in the brain and the activation of astrocyte cell fingers that produce convective forces.

In one example, pulses 50 may create an intensity spatial peak temporal average (ISPTA) of around 650-10,000 mwatts/cm$^2$. A typical treatment session may apply ultrasonic pulses 50 to a target area for around 30-90 minutes to simulate a complete deep sleep period.

Extensive research into the heating of tissue from ultrasound exposure has led to the development of several guideline relationships that describe the safe exposure duration for a given temperature increase. Specifically, for temperature increases of 6° C. or less (which is the temperature at which non-reversible tissue changes occur) the following relationship has been derived for non-fetal tissue:

$\Delta T < 6 - (\log t)/0.6$ where $\Delta T$ is the maximum expected temperature rise above normal body temperature (37° C.), and t is the duration in minutes that the exposure can be maintained without incurring damage.

From this relationship, and the ultrasound parameters used for LIFUP, the safe exposure time can be estimated. In use, the LIFUP system creates temperature rises within the brain of less than 0.5° C., which is the lower limit of the MRI thermography techniques used. Conservatively, if $\Delta T$ is set to 0.5, solving for t yields an exposure time over 16 hours. Thus, unlike other ultrasound systems which are used to produce thermal lesions within the brain tissue, for instance, to treat Parkinson's disease, the LIFUP system disclosed herein can be considered safe over extended treatment times.

While the current embodiments show a single transducer on one side of the head, positioned at the so-called temporal window, there are other transducer configurations which can provide advantages in certain situations. For instance, positioning the transducers bilaterally on either side of the skull affords the possibility of using one of the transducers as a receiver while the other is a transmitter. In this way, the conduction of the ultrasound energy into the skull can be independently ascertained, without the need for MRI verification. One of the transducers can specifically be designed as a receiver, or both transducers can be identical in design, since piezoelectric transducers are reciprocal in nature. The advantage of a specifically designed receiver is that it could, for instance, be unfocussed, so that it has a broader range of coverage within the skull. An advantage of this bilateral approach is that it could be used to verify transmission without the use of an MRI system.

Example Procedure

One example process applies transcranial ultrasound treatment from ultrasonic waves 30 generated by TNS 100 to treat mild cognitive impairment (MCI) or dementia. In one example, patients showed cognitive decline with mild cognitive impairment (Clinical Dementia Rating stage 0.5) through moderate dementia CDR stages 1 and 2.

In one example, patients are given a lumbar puncture for ABeta 42 and Tau proteins for Alzheimer's Spectrum. The lumbar puncture is performed once at entry. Patients were given an advanced MRI of the brain to include volume measurement of the hippocampus, ASL perfusion scans and MRS of prefrontal, precuneus, and hippocampus.

On entry, patients may have CDR stage of at least 0.5 and at least one abnormal imaging biomarker. Baseline, two months (completion) testing may include the Quick Dementia Rating System (QDRS) for staging and the following battery of tests:
  the Repeatable Battery for Assessment of Neuropsychological Status (RBANS),
  Standardized 25 foot timed gait test
  the Nine Hole Pegboard Test,
  Montreal Cognitive Assessment Test versions 1, 2, 3 (MOCA),
  Brain imaging will be repeated at completion that include an anatomical scan (MPRAGE), ASL and BOLD and MRS in the targeted network.

CSF studies demonstrated good sensitivity and specificity for MCI and dementia of the Alzheimer's type (ref 5). MRI volumetrics, perfusion scans and MR spectroscopy have shown to be good discriminating value among AD, PDD/DLB and FTLD subgroups and is responsive to change as patient's progress from MCI to dementia.

For patients with amnestic predominant cognitive change, TNS 100 is targeted at the mesial temporal lobe through a trans temporal scalp window. Targeting may include referencing scalp fiducials based on an obtained MRI. A Doppler waveform confirmation may be obtained because of the ability of transcranial Doppler (TCD) to record Doppler signals from the posterior cerebral artery that runs medial to the mesial temporal lobe.

TNS 100 may target the temporal parietal region for Logopenic Alzheimer's. TNS 100 may target other regions for Parkinson's depending on the clinical requirements. TNS 100 may target area 6 for severe motor symptoms or the frontal lobe or mesial temporal lobe for dysexecutive and amnestic syndromes, respectively.

Alzheimer ultrasonic procedures may place the patient in a quiet room in a post op area of a certified outpatient surgical center where medical staff with a limited EEG montage monitor eye movements, muscle tone, frontal and occipital EEG for tracking sleep stages. The media staff also may monitor patient EKG and pulse oximetry.

Techniques used for promoting sleep in the office may include mild sleep deprivation, holding off on stimulants, and potentially using sleep inducing medication. Slow wave sleep is targeted. TNS 100 applies 30-90 minutes of ultrasound to the patient with a two megahertz probe affixed to the headset with parameters set within FDA safety limits for diagnostic ultrasound. The patient is allowed to wake up after the treatment session and may be discharged when fully awake and in the care of a responsible adult. In one example, ultrasonic energy is applied to the patient for 30-90 minutes and is repeated once per week for around two months.

Regions of the brain where ultrasonic waves 30 are applied may depend on the network target. For example with amnestic predominant Alzheimer's disease TNS 100 may direct waves 30 to a region of interest (ROI) on the mesial temporal lobe and evaluate connectivity for output network nodes such as the anterior nucleus of the thalamus and the precuneus. For logopenic forms of Alzheimer's, TNS 100 may direct waves 30 to the temporal parietal region with a ROI in this region and connectivity analysis of frontal-parietal connections.

Example Transducer Systems

Figure 1G:
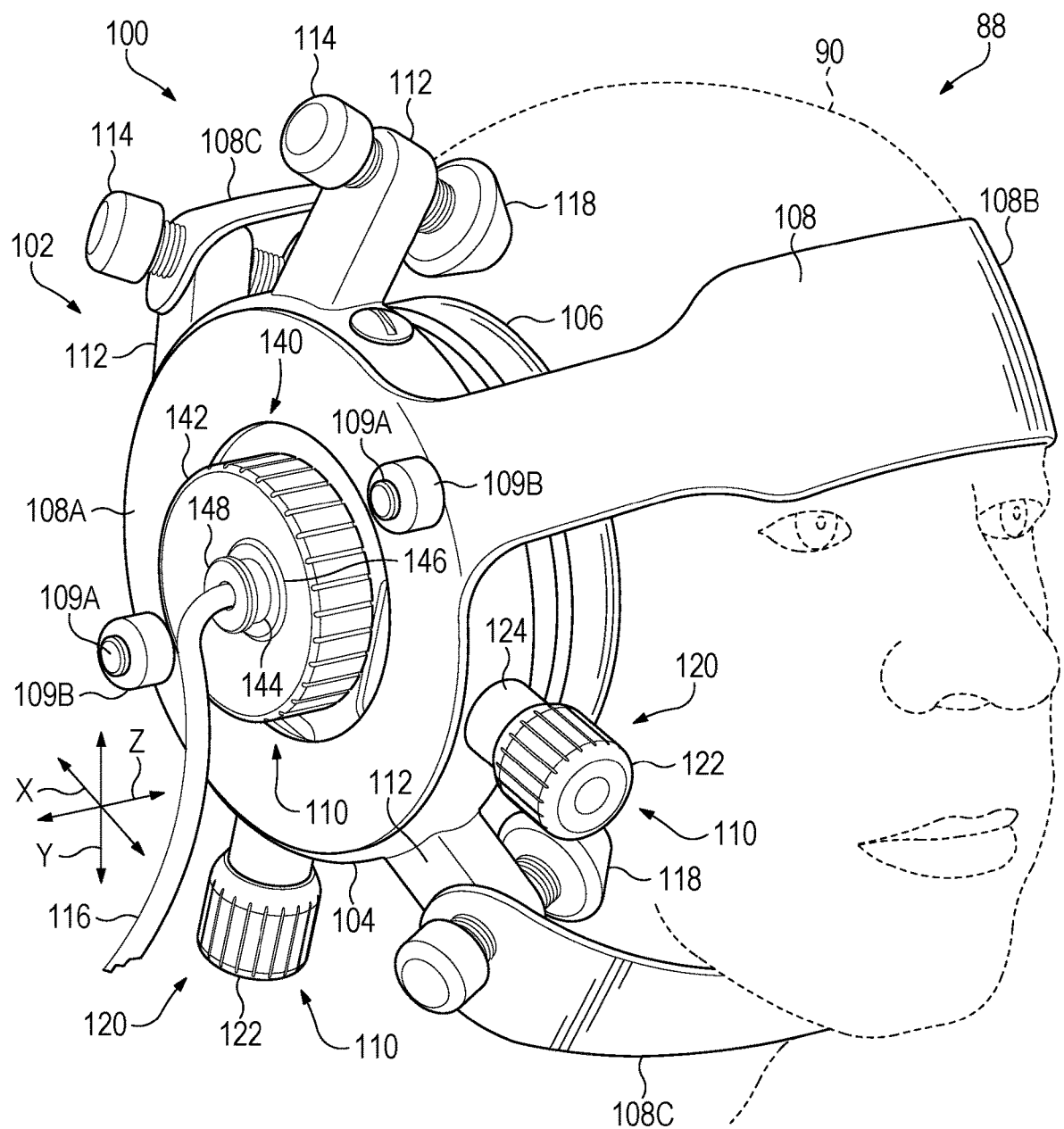
FIG. 1G is a perspective view of a focused ultrasonic transducer navigation system used for treating degenerative dementia.

FIG. 1G shows a perspective view for one example, ultrasonic Transducer Navigation System (TNS) 100. TNS 100 may be attached to a patient 88 and may apply ultrasonic energy to precise target locations within patient 88 associated with different types of degenerative dementia including Alzheimer's disease. The explanation below discusses the specific example of using TNS 100 to apply ultrasonic energy to a target location within head 90 of patient 88 such as the hippocampus and/or parahippocampal gyrus regions. However, it should be understood that TNS 100 may apply any type of sonic, magnetic, or any other alternative energy to any target location within any body part of patient 88. TNS 100 may be used on human patients or animal patients.

A housing assembly 102 comprises an outer housing 104 attached to a movable inner housing 106. A transducer (see FIG. 4) may be located within inner housing 106. A power cable 116 may attach to the transducer and extend up through inner housing 106 and outer housing 104. A first vertical strap 108C attaches to elevating screws 114 and wraps around the top of head 90 and underneath the chin of patient 88. A second horizontal strap 108 includes a ring shaped section 108A that attaches to an outside surface of outer housing 104 via screws 109A and nuts 109B and a headband section 108B that wraps around the front over the eyes and back of head 90. While shown attached to head 90, it should be understood that straps 108, or other attachment devices, may attach housing assembly 102 to other body parts of patient 88. The housing assembly 102 may be attached by straps 108 to the right side or left side of head 90 to apply ultrasonic energy to targets on inside either side of head 90.

Three housing arms 112 may extend radially out from sides of outer housing 104. Elevating screws 114 may rotatably extend through housing arms 112 and may include elastomeric cushions 118 that press up against head 90. Elevating screws 114 may be rotated downward pressing against head 90 to reduce some of the compressive force of inner housing 106 against head 90. This will be described in more detail below.

An alignment system 110 may move the transducer within inner housing 106 into different x, y, and/or z positions with respect to head 90. The x position may refer generally to front to back positions with respect to head 90, the y position may refer generally to top to bottom positions with respect to head 90, and the z position may refer generally to a transverse inside to outside, or left to right positions, with respect to head 90.

If TNS 100 were attached on the top of head 90, the x position may refer to front to back positions with respect to head 90, the y position may refer to the left to right or side to side positions with respect to head 90, and the z position may refer to the transverse inside to outward or top to bottom positions with respect to head 90.

Alignment system 110 may comprise side adjustment assemblies 120 and a top adjustment assembly 140 that have the unique ability to move the transducer within inner housing 106 in different x, y, and z directions while TNS 100 remains attached to head 90 of patient 88. This allows more precise alignment of the transducer with a target location within head 90. Alignment system 110 also may provide quicker and more accurate reattachment of the TNS to head 90 to a same relative position with respect to the target location. This allows TNS 100 to be repeatedly reattached during multiple ultrasonic therapy sessions without using a MRI device to relocate the target location.

Side adjustment assemblies 120 each include a side adjustment knob 122 that rotatably attaches to a side extension 124 that extends radial out from the side of outer housing 104. Top adjustment assembly 140 includes a top adjustment knob 142 that is rotatably attached to outer housing 104. A threaded ring 146 extends out through the middle of top adjustment knob 142. A top end 144 of a transducer lid extends out through threaded ring 146 and a cap 148 inserts into a center cavity of the top end 144 of the transducer lid. Cap 148 operates as a wire guide for receiving cable 116 and also operates as a stop for top end 144 of the transducer lid.

Figure 1H:
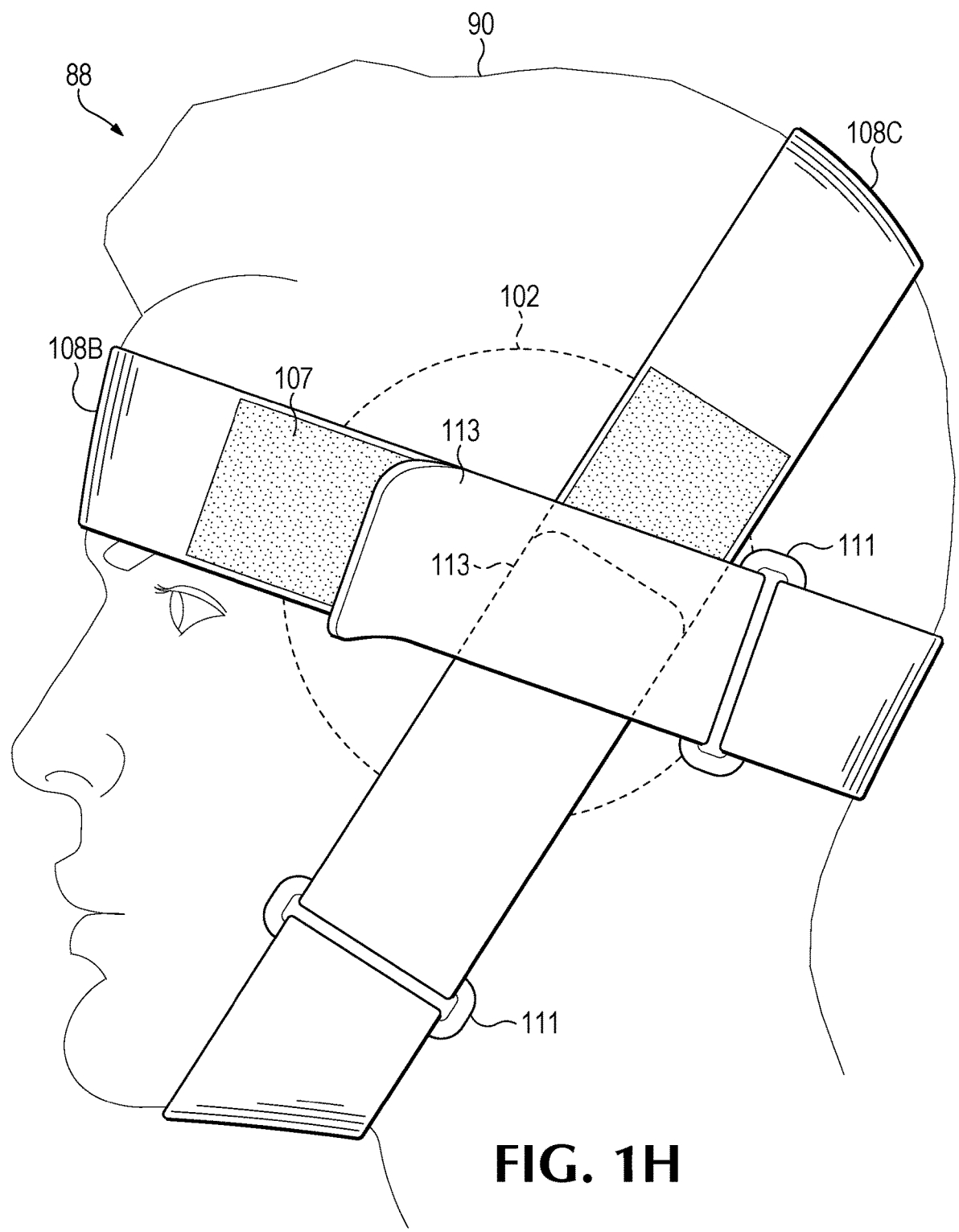
FIG. 1H is a side view of straps used for attaching the ultrasonic transducer navigation system to a patient.

FIG. 1H shows opposite ends 113 of strap sections 108B and 108C. In one example, a hook and eye type material 107, such as Velcro®, may be attached to the ends of strap 108. For example, ends 113 of straps 108 may include a hook material and may be fed through cinches 111. Strap ends 113 are pulled to hold housing assembly 102 snugly against the opposite side of head 90. The hook material on strap ends 113 is then attached to eye material 107.

Other attachment assemblies may be used for attaching ends 113 of straps 108. For example, hook and eye buckles or ratchet buckles may be used on ends 113 of straps 108. In yet another example, strap sections 108B and 108C may be formed from elastic materials that are stretched and held compressively over head 90. Of course other attachment devices also may be used.

In one example, straps 108 may be made out of leather. However, any material may be used that can securely hold housing assembly 102 against patient 88. As just discussed, straps 108 may alternatively be an elastic plastic, rubber, or cloth material. Straps 108 may be available in multiple lengths and sizes to attach to various patient head sizes and patient body parts for small children to large adults.

Figure 2:
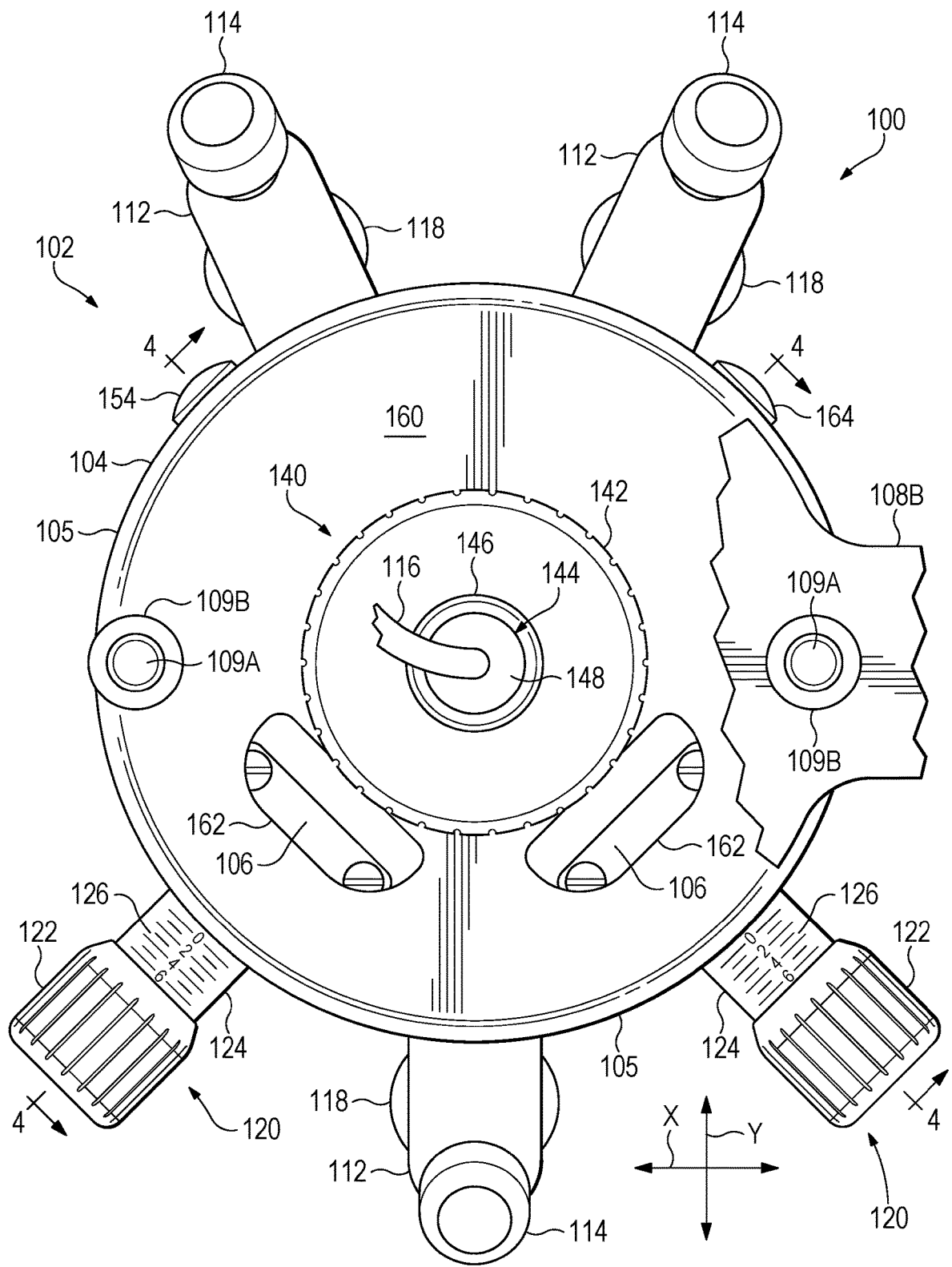
FIG. 2 is a side view of the ultrasonic transducer navigation system.

FIG. 2 shows a side view of TNS 100. Outer housing 104 comprises a circular outside surface 160 with two openings 162 that show a portion of inner housing 106 attached to side adjustment assemblies 120. Housing arms 112 extend radially out from the sides of outer housing 104 and operate similar to a tri-pod allowing TNS 100 to be steadily supported by elevating screws 114 on varying elevational locations on head 90.

Side adjustment assemblies 120 may each include inner adjustment screws (see FIG. 4) that have first ends that attach to inner housing 106 and second ends that attach to side adjustment knobs 122. Two threaded stationary pins 164 are located on sides of outer housing 104 opposite adjustment assemblies 120. Pins 164 slidingly insert into sides of inner housing 106 opposite the sides attached to side adjustment assemblies 120.

Side adjustment knobs 122 can be rotated in both clockwise and counterclockwise directions. For example, rotating either one of side adjustment knobs 122 in a clockwise direction may cause the inner adjustment screw to rotate inward. The inner adjustment screw in turn moves inner housing 106 away from side adjustment assembly 120 and toward an opposite end of outer housing 104 and toward one of pins 164. Rotating one of side adjustment knobs 122 also causes knob 122 to move radially inward over an outside surface of side extension 124 and toward an outside perimeter 105 of outer housing 104.

Rotating any combination of side adjustment knobs 122 in an opposite counter clockwise direction may cause the inner adjustment screws to rotate outward. The inner adjustment screw in turn may pull inner housing 106 toward side adjustment assembly 120 and away from the opposite end of outer housing 104 where pin 164 is located. The counter clockwise rotation also may cause side adjustment knob 122 to move radially outward over the outside surface of side extension 124 away from outside perimeter 105 of outer housing 104.

Gradations 126 are imprinted on the outside surface of side extensions 124. In one example, each gradation 126 may be spaced apart one millimeter (mm). Gradations 126 in combination with side adjustment knobs 122 operate as micrometers identifying distances of x and y movement of the transducer contained inside of inner housing 106. For example, after TNS 100 is attached to the head of the patient, side adjustment knobs 122 may be rotated to adjust the location of the transducer so a focal point of ultrasonic energy is directed precisely over a target area inside of the brain of the patient.

Top adjustment knob 142 is co-centrically positioned on top of outer housing 104. Threaded ring 146 is concentrically positioned within top adjustment knob 142 and cap 148 is concentrically positioned within top end 144 of the transducer lid and over threaded ring 146. Rotating top adjustment knob 142 in a first direction may move top end 144 of the transducer lid in an upward z direction away from the head of the patient. Rotating top adjustment knob 142 in a second opposite direction may move top end 144 of the transducer lid in a downward z direction toward the head of the patient.

Figure 3:
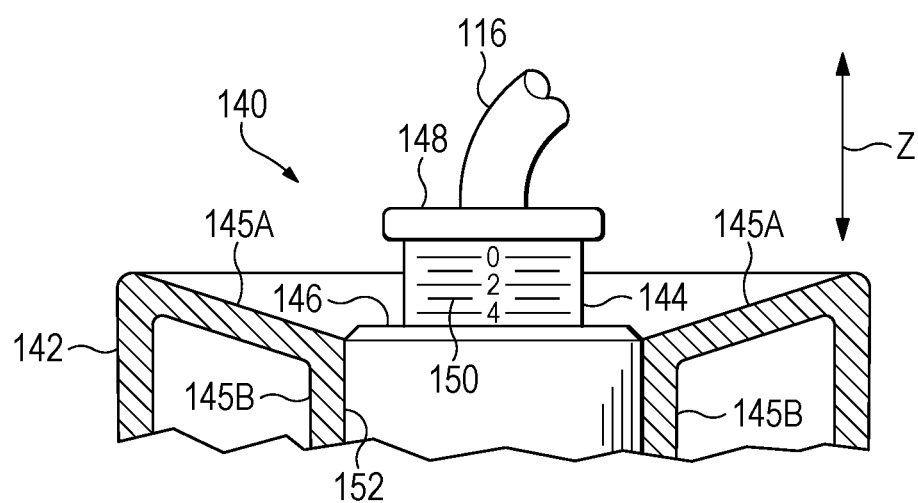
FIG. 3 is a partial side sectional view of a top adjustment assembly.

FIG. 3 shows a partial side cut away view of top adjustment assembly 140. Top adjustment knob 142 has an oppositely inclining top wall 145A and an inner side wall 145B that form an inner hole 152 that receives threaded ring 146. Screws (not shown) may insert into side walls 145B and rigidly couple adjustment knob 142 to threaded ring 146.

Rotating top adjustment knob 142 in the first direction also rotates threaded ring 146 causing top end 144 of the transducer lid to move in an upward z-direction away from the head of the patient. Rotating top adjustment knob 142 in the second opposite direction also rotates threaded ring 146 in the same direction moving top end 144 of the transducer lid in a downward z-direction toward the head of the patient.

Gradations 150 may be imprinted on an outside surface of top end 144 of the transducer lid. In one example, gradations 150 also have one millimeter spacing. Gradations 150 in relation to the location of rotating knob 142 also operate as a micrometer identifying an amount of movement of the transducer in the z direction.

Figure 4:
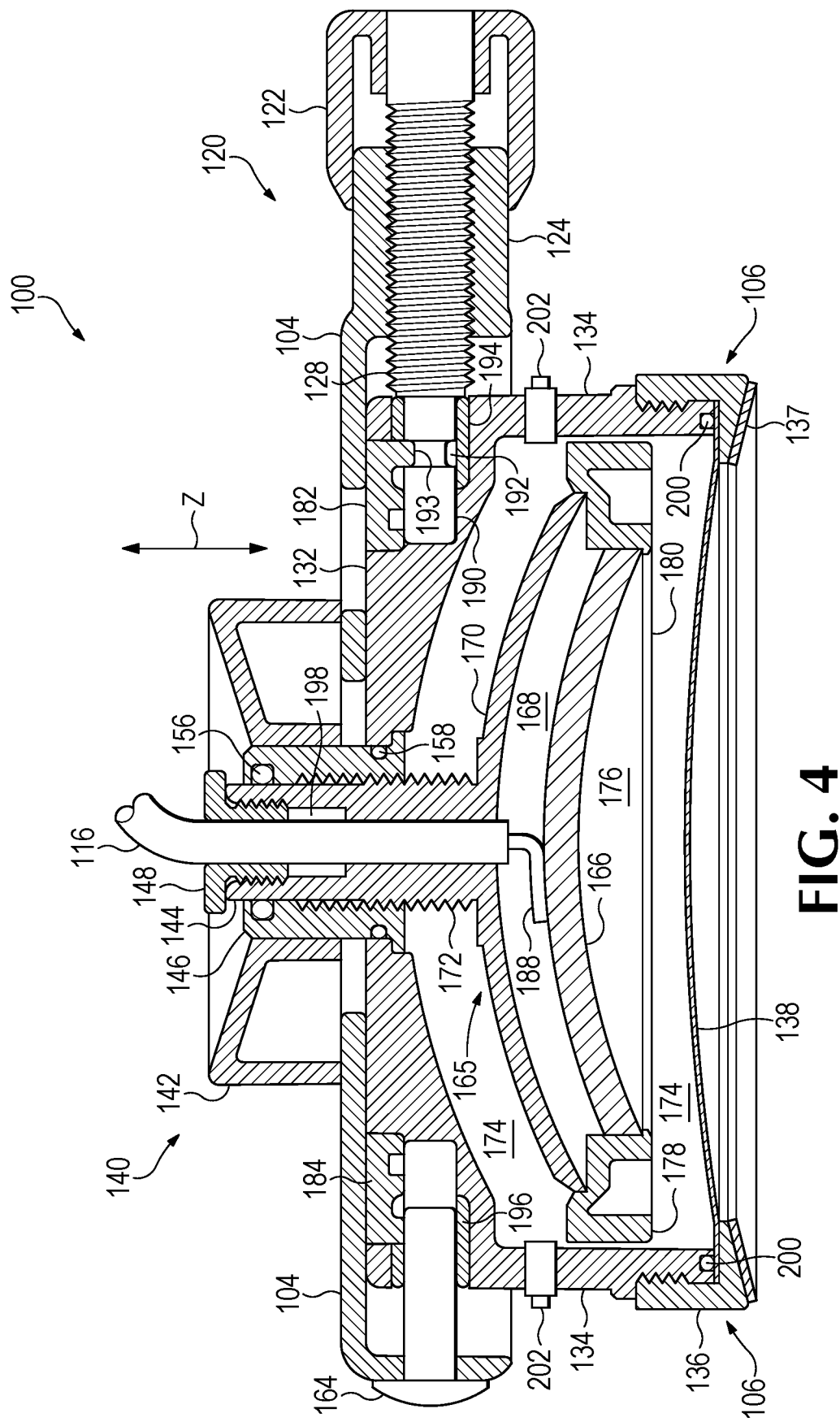
FIG. 4 is a front sectional view of the ultrasonic transducer navigation system.

FIG. 4 shows a front sectional view of TNS 100. Inner housing 106 comprises a top wall 132, side walls 134, a membrane clamping ring 136, and a hypo-allergenic flexible membrane 138 that together form a sealed inner housing chamber 174 configured to retain a transducer assembly 165. In one example, chamber 174 may be sealed and filled with degassed oil or water to improve efficiency of transferring the ultrasound waves through the skull and brain and into the target location.

Membrane 138 may be formed of a plastic or rubber material and is configured to elastically press up against the head of the patient. The threaded connection of clamping ring 136 to side walls 134 allow membrane 138 to be detached from the rest of inner housing 106. A cushion 137 may be glued to the bottom of clamping ring to increase comfort and conform around irregularities on the surface of the head of the patient. After completing the ultrasonic therapy sessions for a patient, membrane 138 may be removed and replaced with a new membrane for a next patient. A layer of gel may be spread over an outside surface of elastic membrane 138 and may maintain a continuous seal between membrane 138 and the head of the patient as will be discussed in more detail below in FIG. 8.

Transducer assembly 165 comprises a transducer 166 located between a transducer lid 170 and a transducer base 178. A space between transducer 166 and transducer lid 170 forms an airtight sealed back cavity 168. A space between transducer 166 and transducer base 178 forms a sealed front cavity 176 configured to retain water. A single transducer 166 is shown in FIG. 4. However, inner housing 106 and transducer assembly 165 may be configured to retain any transducer shape and any number of transducers, such as circular transducers and multi-transducer arrays.

Transducer lid 170 includes a neck 172 that extends up inner housing 106, outer housing 104, and threaded ring 146. As shown above, top end 144 of transducer lid 170 extends up through a top end of threaded ring 146 and includes a threaded internal hole 198 configured to threadedly receive cap 148. Left hand threads may be formed on the outside surface of cap 148 to prevent cap 148 from being unscrewed if it bottoms out against the top of ring 146. A threaded outside surface of neck 172 is configured to threadedly engage with a threaded inside surface of ring 146. Cable 116 extends through a hole in the center of neck 172 and wires from cable 116 are coupled to transducer 166.

As mentioned above, rotation of top adjustment knob 142 in a first direction rotates threaded ring 146 around threaded neck 172 moving transducer assembly 165 in a first upward z direction toward top wall 132 of inner housing 106. Rotation of top adjustment knob 142 in the opposite direction rotates threaded ring 146 around threaded neck 172 in the opposite direction moving transducer assembly 165 in a second downward z direction toward membrane 138. Cap 148 operates as a stop preventing top end 144 of transducer lid 170 from moving down below a top end of threaded ring 146.

An O-ring 156 is located between threaded ring 146 and top end 144 of transducer lid 170. An O-ring 158 is located between threaded ring 146 and the inside surface of a hole formed in top wall 132 of inner housing 106. O-rings 156 and 158 are configured to maintain a watertight or oil tight seal within chamber 174 while threaded ring 146 is rotated around transducer neck 172. An O-ring 200 may be located between the bottom end of side walls 134 and membrane clamping ring 136 to provide a watertight or oil tight seal along the bottom end of cavity 174.

Inner housing 106 may be made of a clear see-thru plastic that allows a technician to visually detect any air bubbles that may exist in the oil or water within chamber 174. Two compression nozzles 202 may be mounted within side walls 134 of inner housing 106. Compression nozzles 202 may be used for filling chamber 174 with water or oil and bleeding air bubbles out of chamber 174, similar to bleeding air out of vehicle braking systems. For example, water may be forced into a first one of nozzles 202. A second one of nozzles 202 may be depressed or unscrewed to bleed water and air bubbles from chamber 174. An indication that most or all of the air bubbles are removed may be provided when only water bleeds out of second nozzle 202. Inner housing 106 may be shaken during the bleeding process to promote the air bubbles to exit out of second nozzle 202.

Each side adjustment assembly 120 may include an inner adjustment screw 128 that forms a head 190 at a front end and is attached to a side adjustment knob 122 at a back end. A sleeve 194 is inserted into a hole formed in the side of inner housing 106. Screw head 190 inserts and rotates inside of sleeve 194. An alignment guide 182 is attached to inner housing 106 and includes a lip 193 that seats into a groove 192 formed in screw head 190. A sleeve 196 inserts into a hole formed in an outer opposite side of inner housing 106. A front end of threaded stationary pin 164 slidingly inserts into sleeve 196 and a back end of pin 164 threaded and rigidly attaches to outer housing 104. An alignment guide 184 attaches to inner housing 106 and slidingly presses against a top side of the front end of pin 164.

Threads are formed on an inside surface of a hole formed inside of each side extension 124 and engage with threads on screw 128. Rotating side adjustment knob 122 in a first direction rotates screw 128 and moves head 190 in a forward direction. Screw head 190 pushes inner housing 106 away from side extension 124 toward the opposite side of outer housing 104 while sleeve 192 on the opposite end of inner housing 106 slides further over the front end of pin 164.

Rotating side adjustment knob 122 and screw 128 in an opposite direction move head 190 in a reverse direction. Head 190 pulls lip 193 and attached inner housing 106 toward side extension 124 while sleeve 196 on the opposite side of inner housing 106 moves further out from the front end of pin 164.

Alignment guides 182 and 184 allow inner housing 106 to move into any x and y position. For example, adjustment screws 128 may move inner housing 106 into different positions. Alignment guides 182 may slide over groves 192 on screw heads 190 and alignment guides 184 may slide over pins 164 allowing movement of inner housing 106 into any x and y position within outer housing 104.

Operation Overview

Referring to FIGS. 1-4, patient 88 may have focused ultrasonic transducer navigation system (TNS) 100 strapped onto head 90 while undergoing an MRI-assisted positioning procedure. An administrator controlling an electronic power source stimulator may be in a nearby room which is safe from the magnetic field produced by the MRI device. The administrator may use a functional MRI (fMRI) method that shows images from inside of the brain of patient 88 and shows a target spot specific for treatment of a particular disorder.

TNS 100 may send a Low Intensity Focused Ultrasound Pulse (LIFUP) into the brain which can be seen and recorded on an fMRI console screen as a change in a BOLD signal. The resulting location of the ultrasonic pulse is measured relative to the spot targeted for treatment. Alternatively, the location may be verified by fMRI sequences that measure small temperature changes within the brain occurring as a result of the LIFUP stimuli.

The administrator slides patient 88 out from under the MRI device and adjusts side adjustment knobs 122 and top adjustment knob 142 (micrometer dials) to move the focus of the LIFUP generated by transducer 166 to the desired target location. The MRI comparison procedure is repeated until transducer 166 generates an ultrasonic pulse directly on the center of the target location in all three x, y, and z planes. TNS 100 is then used to perform an ultrasonic treatment.

A medically approved pen is used to mark a portion of a circle around the perimeter of inner movable housing 106 and on the head of patient 88. In one example, inner housing 106 may be made from a clear plastic material. Marking the head with the ink pen enables subsequent treatments to be administered in the office of a doctor or technician without having to use an expensive MRI device to repeatedly realign TNS 100. Thus the time and cost per treatment may be significantly reduced.

The three elevating screws 114 may be adjusted to any size and shape of head 90 and in one example may use comfortable STERalloy Elastomeric cushions 118. Elevating screws 114 raise membrane 138 slightly off head 90 to facilitate the free movement of inner moveable housing 106 in the x and y planes. Side adjustment assemblies 120 may be used to align inner housing 106 with the circle previously marked on the head of patient 88 centering ultrasonic energy generated by transducer 166 into the center of the target within the brain.

When the x and y planes are on target, elevating screws 114 are backed off to lower membrane 138 more firmly against head 90. A gel may be applied to membrane 138. The gel may maintain a contact layer between membrane 138 and head 90 while membrane 138 is moved to different x and y positions. The gel layer may prevent an air gap from forming between membrane 138 and head 90 that could reduce efficiency of the focused ultrasound waves output by transducer 166.

After completion of the LIFUP treatments, the STERalloy elastomeric cushions 118, membrane clamping ring 136 and membrane 138 may be replaced. This may prevent allergies or other undesirable effects from being transferred to other patients. The LIFUP procedure may be welcomed by the insurance companies as compared to surgery which may be more expensive and higher risk.

Initial Alignment and Treatment

During the initial MRI alignment procedure described above, the focal point of ultrasonic energy output from transducer 166 is aligned as closely as possible to the center of the target location. This allows more tolerance when realigning TNS 100 during subsequent treatments.

Figure 5:
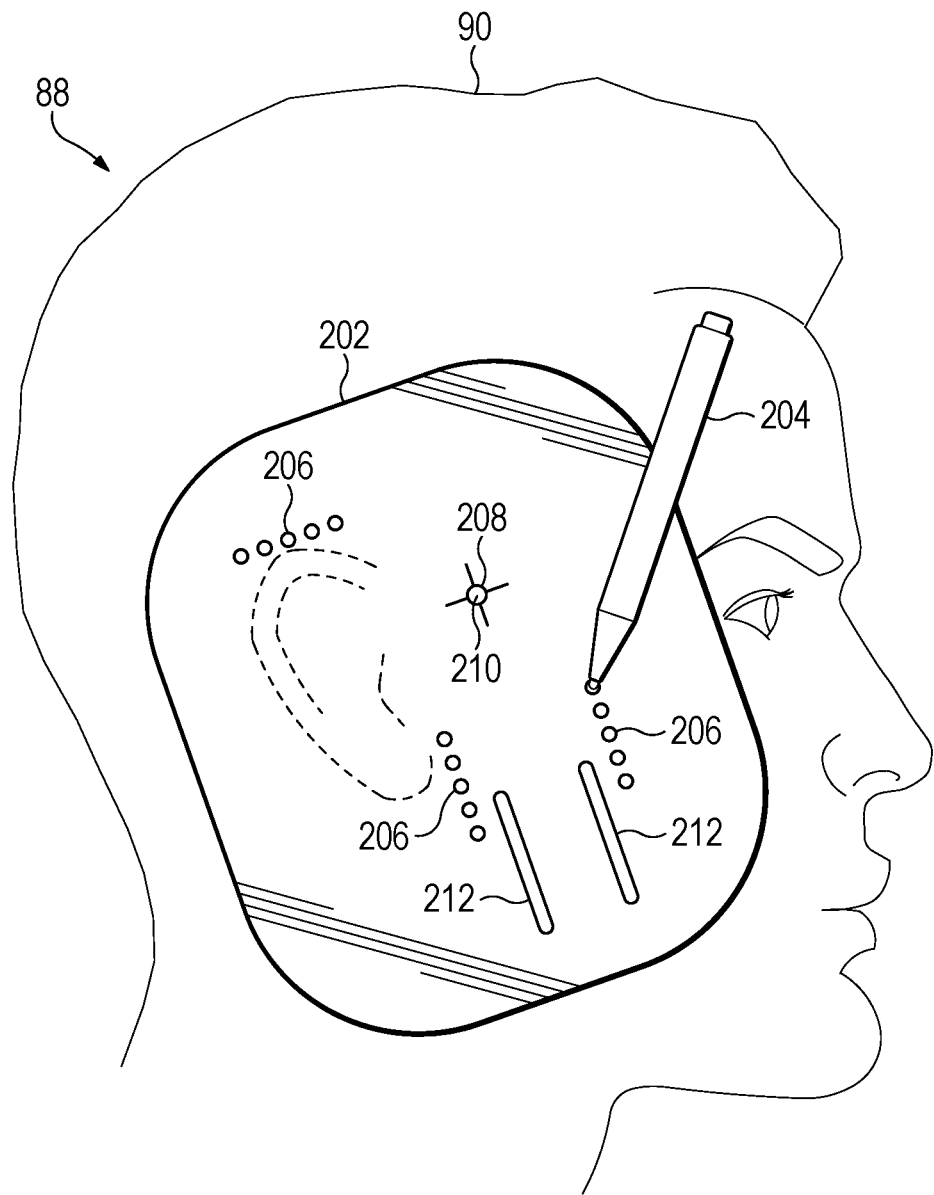
FIG. 5 is a side view of a template used for aligning the ultrasonic transducer navigation system.
Figure 6:
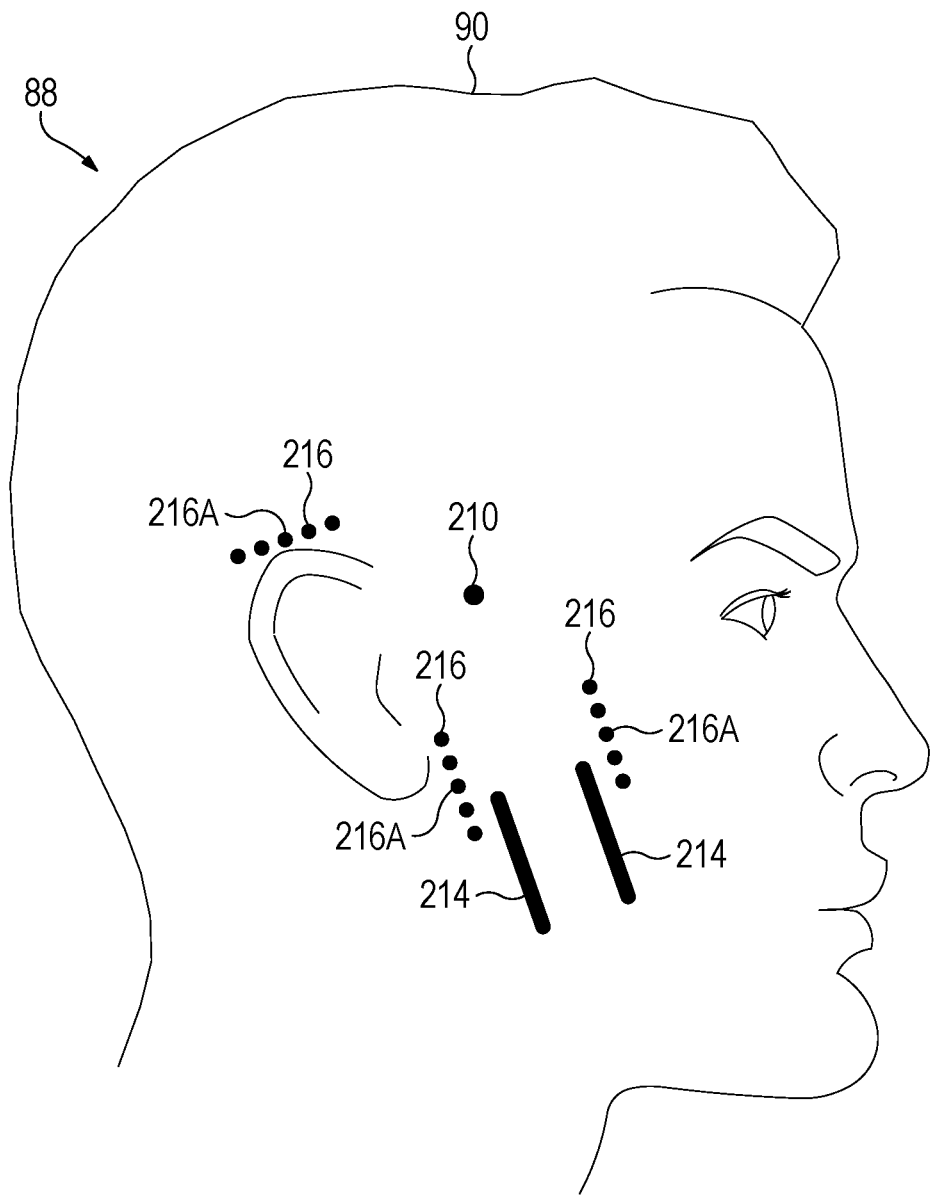
FIG. 6 shows reference marks created using the template of FIG. 5.

Referring to FIGS. 5 and 6, patient 88 may lie on their side and head 90 may be shaved in the installation location for TNS 100. A target mark 210 is applied to head 90 with an ink pen 204. A template 202 includes a hole 208 that is aligned over target mark 210, holes 206 that are aligned with the outside perimeter of inner housing 106, and two slots 212 that are aligned with one of housing arms 112. Template 202 may be made from a clear semi-rigid plastic material.

Template 202 is placed against head 90 so hole 208 aligns over target mark 210 and slots 212 are located in a desired location for one of housing arms 112. While holding template against head 90, ink pen 204 is used to apply reference lines 214 to head 90 through slots 212 and apply reference marks 216 to head 90 through holes 206. Template 202 is then removed. The third middle reference mark in each column of five reference marks 216 is alternatively referred to as a center reference mark 216A.

Figure 7:
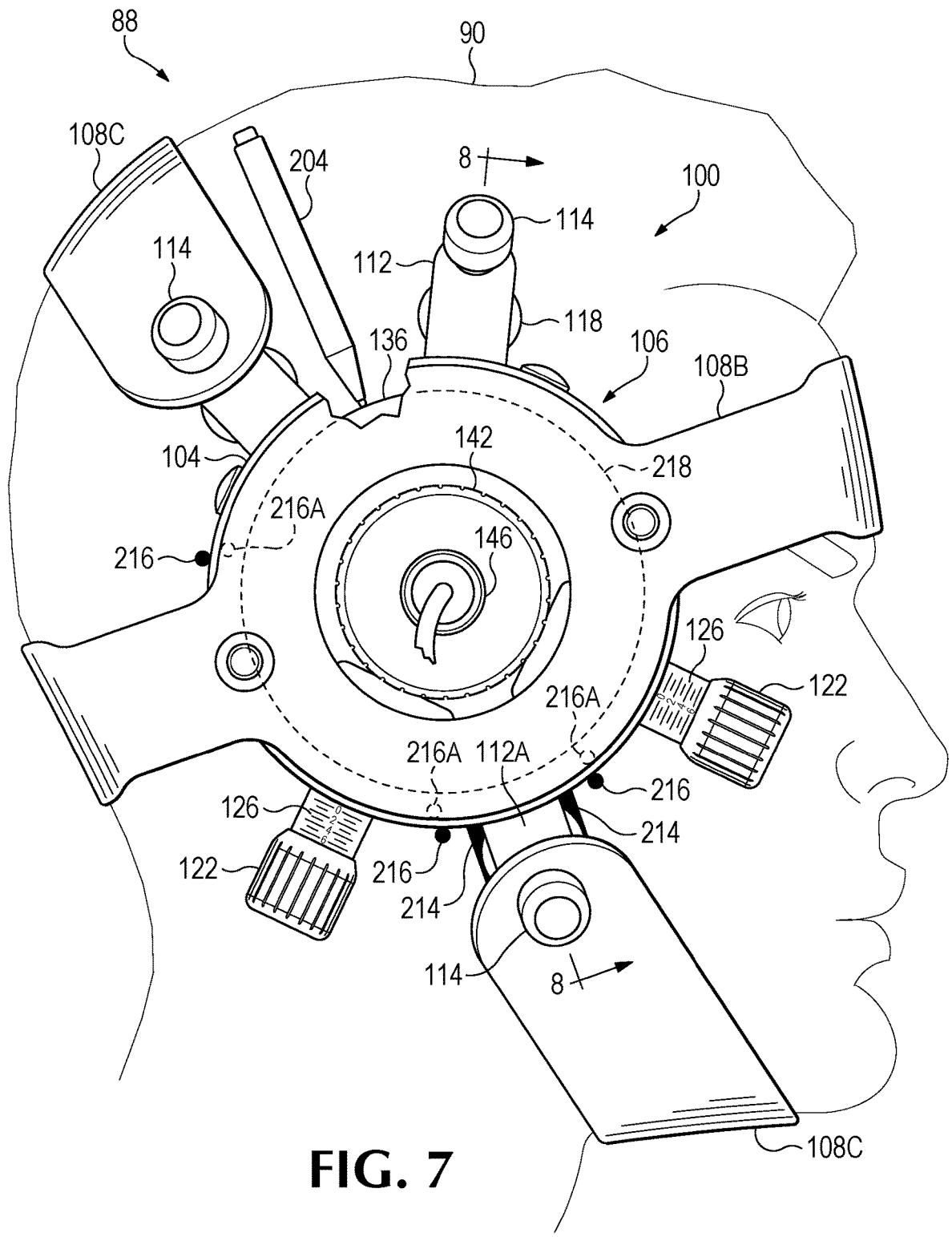
FIG. 7 is a side view of the ultrasonic transducer navigation system attached to a patient.
Figure 8:
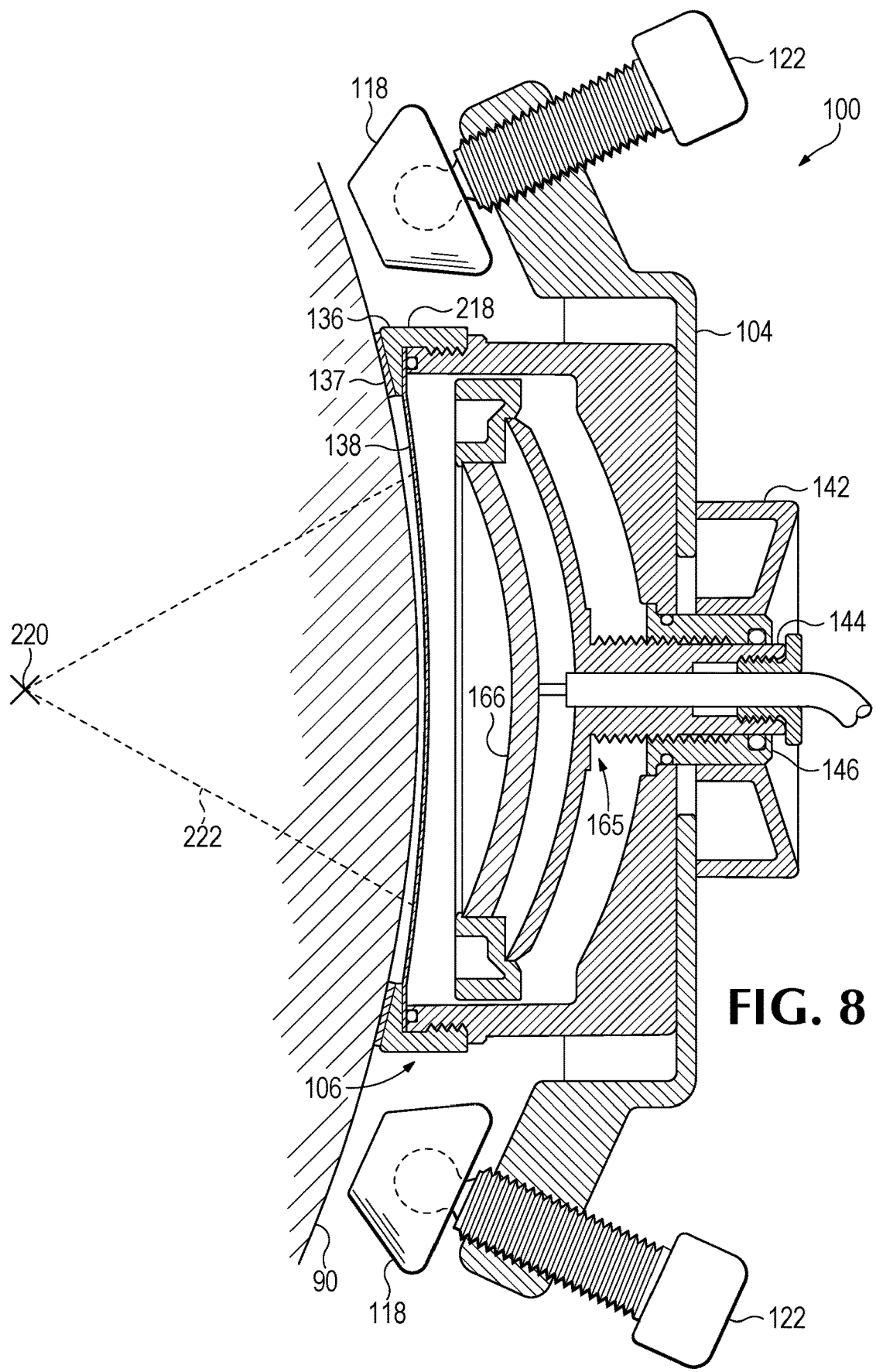
FIG. 8 is a front sectional view of the ultrasonic transducer navigation system shown in a lowered position.
Figure 9:
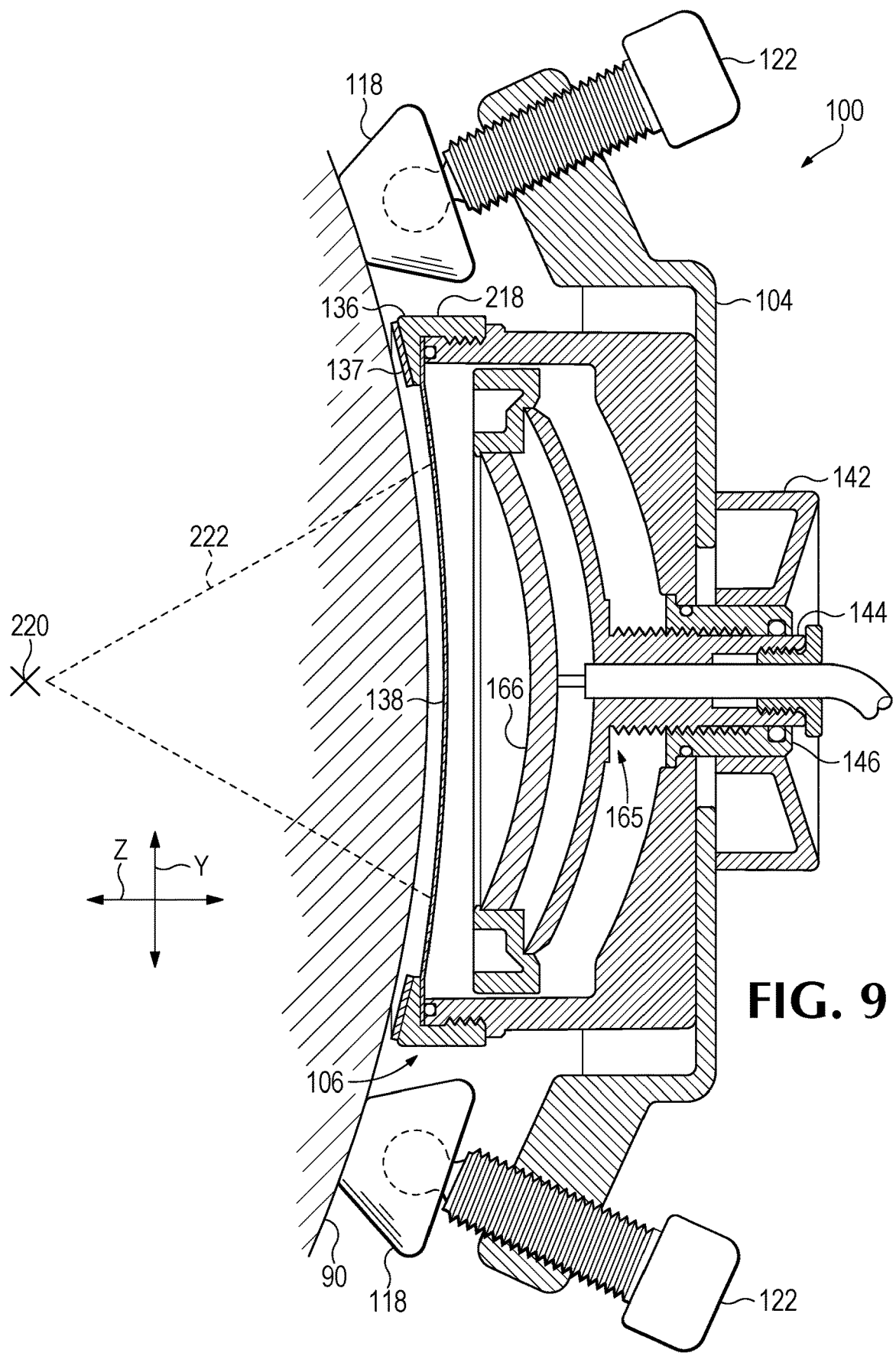
FIG. 9 is a front sectional view of the ultrasonic transducer navigation system shown in a raised position.

FIG. 7 shows a side view of TSN 100 and FIGS. 8 and 9 show front sectional views of TNS 100. FIGS. 7, 8, and 9 shows in more detail how inner housing 106 may be moved into different x, y, and z locations to align with a target location 220.

The x, y and z planes in TNS 100 may be set to nominal positions by setting side adjustment knobs 122 and top adjustment knob 142 each to 6 mm. Gel may be applied to the entire surface of membrane 138 and may be applied so it does not exceed a perimeter 218 of inner housing 106. Perimeter 218 may comprise the outside perimeter of membrane clamping ring 136.

Elevating screws 114 are raised as shown in FIG. 8 so membrane 138 contacts head 90. TNS 100 is aligned on head 90 so center reference marks 216A for each column of five reference marks 216 align with perimeter 218 as shown in FIG. 7. Housing arm 112A is aligned between reference lines 214 as shown in FIG. 7. TNS 100 is held firmly against head 90 to prevent movement and the ends of straps 108 are tightened holding TNS 100 firmly against head 90.

Patient 88 is placed under the MRI device. A pulse 222 from transducer 166 is transmitted into head 90 of patient 88 using the stimulator. The MRI device identifies the pulse location relative to target location 220 in the x and y planes. If the pulse location is off more than 6 mm in the x or y planes, TNS 100 may be removed from head 90 and the three columns of five reference marks 216 used as a guide to realign TNS 100.

For example, reference marks 216 in each column may be spaced a known distance apart. Perimeter 218 of inner housing 106 may be aligned next to a different set of reference marks 216 based on the identified distance between the focal point of ultrasonic pulse 222 and target location 220. Patient 88 then may be placed back under the MRI device and the distance re-measured between the new focal point for the ultrasonic pulse 222 and target location 220. The realignment procedure is repeated until the distance between ultrasonic pulse 222 and target location 220 is less than 6 mm in both the x and y planes.

If the x and y locations of ultrasonic pulse 222 are both within 6 mm of target location 220, elevating screws 114 are screwed down as shown in FIG. 9 to raise inner housing 106 slightly off of head 90. Side adjustment knobs 122 shown in FIG. 7 then may move inner housing 106 inside of outer housing 104. The x and y positions of inner housing 106 are adjusted based on the previously measured distance between the ultrasonic pulse 222 and target location 220.

For example, the MRI device may determine ultrasonic pulse 222 is spaced a distance of 2 mms from target location 220 in an x direction. One of side adjustment knobs 122 may be used to move inner housing 106 2 mms in the x direction. The three elevating screws 122 then may be retracted upward again as shown in FIG. 8 so membrane 138 presses firmly back against head 90. Another ultrasonic pulse 222 is applied to patient 88 and the x and y position of the new pulse measured in relation to target location 220.

The z plane position of inner housing 106 may be adjusted after the x and y positions of ultrasonic pulse 222 are aligned on target location 220. For example, a distance of ultrasonic pulse 222 from target location 220 in the z direction is measured from the MRI images. Top adjustment knob 142 is rotated to move transducer assembly 165 up or down by the measured z distance. Head 90 of patient 88 is then rescanned by the MRI device and the new location of ultrasonic pulse 222 is compared with target location 220. The measurement and adjustment process is repeated until the focal point of ultrasonic pulse 222 aligns over target location 220 in the x, y, and z planes. After alignment of ultrasonic pulse 222, TNS 100 may be checked to see if any gel is visible around perimeter 218 of inner housing 106. Any seeping gel may be wiped clean with a swab.

FIG. 7 shows a pen 204 used for tracing a reference line on head 90 around as much of perimeter 218 as possible. The z setting of TNS 100 may be recorded on a patient identification card. For example, a location of the top end of threaded ring 146 with respect to gradations 150 on top end 144 of transducer lid 170 may serve as the z reference location (see FIG. 3). The reference line traced around perimeter 218 of inner housing 106 may serve as the x and y reference locations.

An initial ultrasonic treatment then may be applied to patient 88 using TNS 100. After completion of the treatment session, TNS 100 may be wiped clean and placed back into a case. The same TNS 100 may be reserved for all subsequent ultrasonic treatments for the same patient.

Subsequent Alignments and Treatments

Reference marks 216, reference line 214 shown in FIG. 6, and the addition reference line drawn around perimeter 218 of inner housing 106 on head 90, may be visually inspected. Any faded reference marks or lines may be redrawn on head 90.

TNS 100 is adjusted to nominal x and y positions by setting side adjustment knobs 122 each to 6 mm. Gel is again applied to the entire surface of membrane 138. Perimeter 218 of inner housing 106 is concentrically aligned as closely as possible with the reference line that was previously traced around perimeter 218. Housing arm 112 in FIG. 7 is also aligned between the reference lines 214. Outer housing 104 extends down about half an inch over inner housing 106, but still allows viewing of outside perimeter 218 of inner housing 106.

TNS 100 is held firmly against head 90 to prevent it from moving while straps 108 is again wrapped and tightened around head 90. If necessary, elevating screws 122 are rotated down from the position shown in FIG. 8 to the position shown in FIG. 9 to raise inner housing 106 enough to slide over head 90 without moving outer housing 104. As mentioned above, the gel on membrane 138 may maintain a contact layer between membrane 139 and head 90 as inner housing 106 is being adjusted in the x and y positions. The elevating screws reduce pressure of membrane 138 against head 90 of patient 88 and allow membrane 138 to remain in contact against head 90 while inner housing 106 is moved into different x and y positions.

The x and/or y positions of inner housing 106 are adjusted until perimeter 218 visually aligns with the circular marked line previously traced around perimeter 218 as shown in FIG. 7. Elevating screws 122 are rotated upward as shown in FIG. 8 until they no longer touch head 90. The z location of inner housing 106 is verified by comparing the z setting on gradation 150 (FIG. 3) with the z setting on the patient identification card. If necessary, top adjustment knob 142 may be rotated to establish the previous z setting on gradation 150.

An ultrasonic treatment may now begin without having to realign transducer 166 using an MRI device. When the ultrasonic treatment is complete, TNS 100 can be wiped clean and placed back into the original case for the next use by patient 88.

TNS 100 is designed to receive a variety of different transducers that can generate ultrasonic energy into the brain or other body parts at a variety of different depths to accommodate a variety of different disorders. For example, TNS 100 may be used for treating psychiatric disorders, such as depression, anxiety, Obsessive-Compulsive Disorder (OCD), bulimia, bipolar disorder, or autism. TNS 100 also may be used to treat a variety of neurological disorders, such as epilepsy, Parkinson's, Alzheimer's, and other dementias, coma, and brain injury. TNS 100 also may be used to treat medical conditions, such as high and low blood pressure, obesity, and endocrine and immunological disease; and perform functional diagnostics of brain circuits.

Alternative Transducer Navigation System

Figure 10:
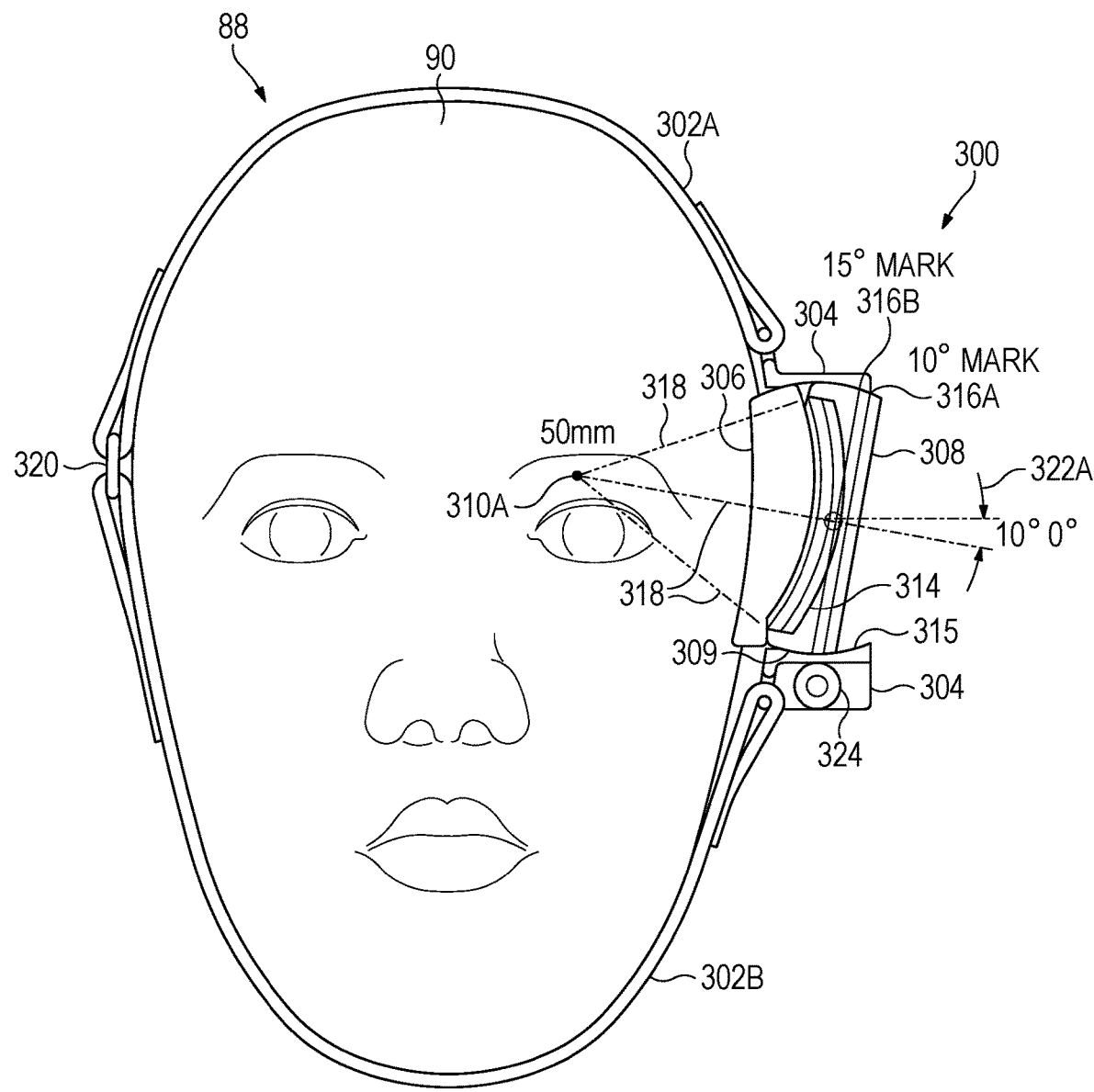
FIG. 10 is a front view of another version of a transducer system used for treating degenerative dementia.
Figure 11:
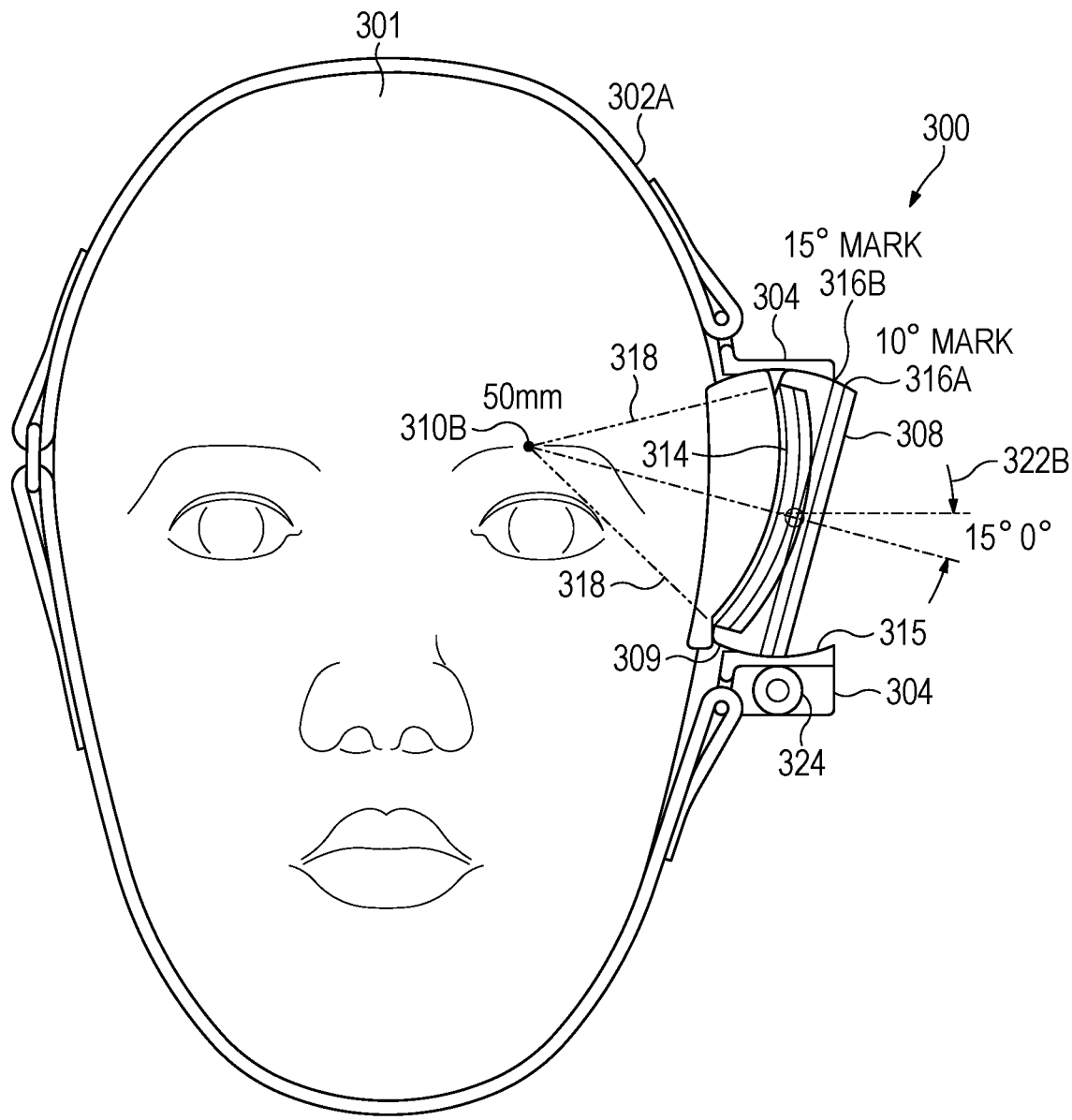
FIG. 11 is another front view of the transducer system shown in FIG. 10.
Figure 12:
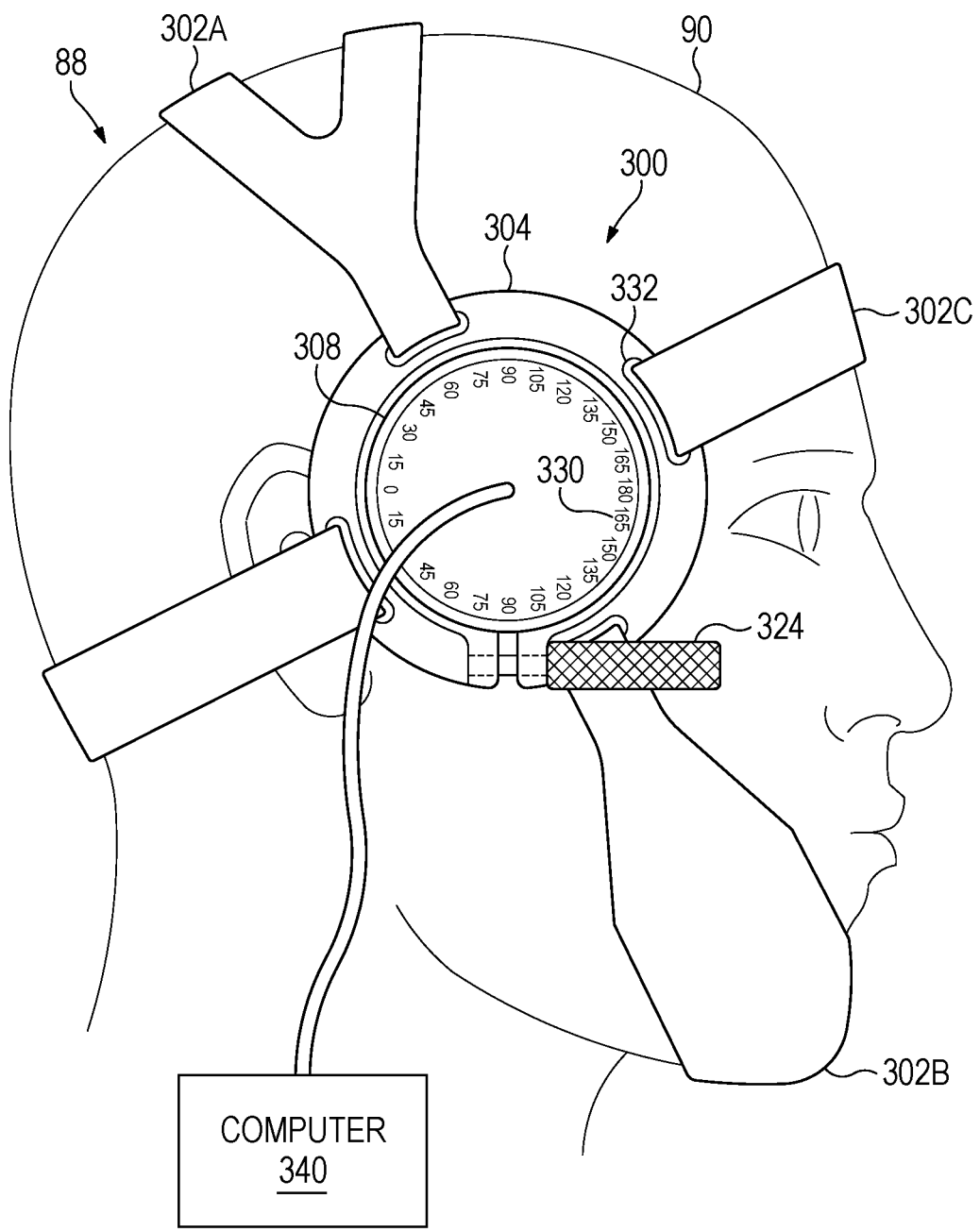
FIG. 12 is a side view of the transducer system shown in FIG. 10

FIGS. 10-12 show an alternative transducer navigation system (TNS) 300 also used for treating degenerative dementia. FIG. 10 is a front view of TNS 300 with a transducer 308 pivoted at 10 degrees, FIG. 11 is a front view of TNS 300 with transducer 308 pivoted at 15 degrees, and FIG. 12 is a side view of TNS 300.

Another transducer navigation system also used for treating degenerative dementia is described in U.S. patent application Ser. No. 15,382,351 filed Dec. 16, 2016, entitled: Stereotactic Frame which is incorporated by reference in its entirety.

Referring to FIGS. 10-12, TNS 300 includes a top strap 302A and a bottom strap 302B attaching to opposite upper and lower ends of transducer cradle 304, respectively. A side strap 302C attaches at opposite ends to forward and rearward ends of cradle 304. Upper and lower straps 302A and 320B may be attached at opposite ends via a ring 320.

A transducer casing 308 may retain an ultrasonic wave transducer 314 and have rounded convex outer side walls 309 that fit inside of rounded concave inner side walls 315 of cradle 304. The rounded walls 315 and 309 allow transducer 314 to pivot at different angles 322 inside of transducer cradle 304. In one example, pivot angle 322 can vary from 0 to 15 degrees. However, pivot angle 322 can vary at a wider range of angles depending on the size and diameter of cradle 304 and transducer casing 308.

An operator may loosen knob 324 and push the back of casing 308 to pivot transducer 314. Knob 324 is then tightened to hold transducer 314 at the selected pivot angle 322. A gel pack 306 may attach onto an inside face of transducer cradle 304 and press against the side of head 90. Alternatively, gel pack 306 may attach to an inside surface of transducer casing 308.

Cradle 304 and retained transducer 314 are attached via straps 302 to a particular location on head 90 of patient 88 for treating a target area associated with degenerative dementia. A technician then may pivot transducer 314 within cradle 304 based on the location of focal point 310 relative to the target area within the brain.

A first marking 316A on casing 308 may identify a 10 degree pivot angle 322A and a second marking 316B may identify a 15 degree pivot angle 322B. The technician may press one edge of casing 308 associated with one of markings 330. For example, the technician may press the edge of casing 308 at 30 degree marking 330 so an opposite side of casing 308 at 150 degree marking 330 pivots to first marking 316A creating a 10 degree pivot angle 322A.

The patient 88 may be inserted into an MRI machine and transducer 314 activated to detect the location of focal point 310A relative to the target area in head 90. Based on the location of focal point 310A, the technician may press down on another edge of casing 308 associated with another marking 330 until an opposite side of casing 308 pivots to second marking 316B producing a 15 degree pivot angle 322B. For example, the technician may further pivot transducer 314 so focal point 310B moves into the hippocampus region 34 of the brain as shown above in FIGS. 1A and 1B. The technician then tightens screw 324 to lock casing 308 inside of cradle 304.

If the new focal point 310B hits the target area, the technician records marking 330 indicating the pressed edge of casing 308 and marking 316B indicating the pivot angle 322 created at identified marking 330. The technician then uses markings 330 and 316B to relocate focal point 310B at the same target area for subsequent ultrasonic therapy sessions.

As mentioned above, transducer 314 may be located on the temporal window. However, other multi-array transducer devices and bi-lateral transducer devices may be used for applying ultrasonic waves outside the temporal window. Patient 88 may have several targets in the middle temporal lobe, including the hippocampus and surrounding cortex. The technician may pivot transducer 314 into previously recorded pivot angles 322 for each of the different target areas.

TNS 300 can be operated within an MRI scanner and in one example contains no Ferro magnetic parts that would interfere with MRI magnetic fields. In one example, TNS 300 may include only titanium and plastic parts.

TNS 300 may connect to a computer 340 that programs the pulse rates, pulse durations, and pulse train patterns described above in FIGS. 1E and 1F. Computer 340 may store different ultrasonic pulse patterns for different types of degenerative dementia and different target areas. The technician may select the particular pulse pattern associated with the particular dementia. Computer 340 then turns power to transducer 324 on and off to create the selected ultrasonic beam activation pattern.

Alternative Embodiments

The embodiments described above use a single transducer on one side of the head, positioned at the so-called temporal window. However, other transducer configurations may be used for treating degenerative dementia which can provide other advantages in certain situations. For instance, using an array of transducers, the focal position may be changed electronically, eliminating the need to physically adjust the transducer position. As may be appreciated by one skilled in the art, the transducer may be an annular array, which permits the focal distance to be changed electronically by applying different time delays to each annular element, effectively changing the radius of curvature and thus the focal depth.

The transducer may also be configured as a phased array, and one skilled in the art would appreciate that this would permit the ultrasound beam to be steered with respect to the angle of transmission. In this case, a pattern of time delays is applied across the elements, causing the ultrasound beam to be steered. This may be desirable so as to insonate a region of the brain that would otherwise require a manual angulation of the transducer, which may impede the transmission of ultrasound because the transducer lifts off the skin surface. In either case, the transducer itself may be placed at the temporal window, since this region affords the least loss of energy through the skull.

Finally, a multiplicity of transducer elements may be positioned around the entire skull, and the transmission from each element adjusted with regard to amplitude and phase so as to produce a focal location within the skull at any desired location. The adjustments compensate for the relative positions of the elements, and the attenuation and other acoustical effects of the skull between each element and the desired focal location.

The so-called temporal window is known to those skilled in the art as the region of the skull which is the thinnest and which therefore produces the least attenuation and other undesired effects on the transmission of ultrasound. However, other locations can be used to transmit ultrasound to locations within the brain. For instance, ultrasound has been used to measure the position of the third ventricle within the brain by placing the transducer in the middle of the forehead. Although the skull is thicker there than at the temporal window, it is relatively uniform and thus does not induce large phase variations in the ultrasonic signal. Thus, while there is attenuation from passage through the bone, the focal properties of the ultrasound beam are relatively stable, and thus portions of the brain in the frontal region are readily accessible using the methods described herein.

Hardware and Software

Figure 13:
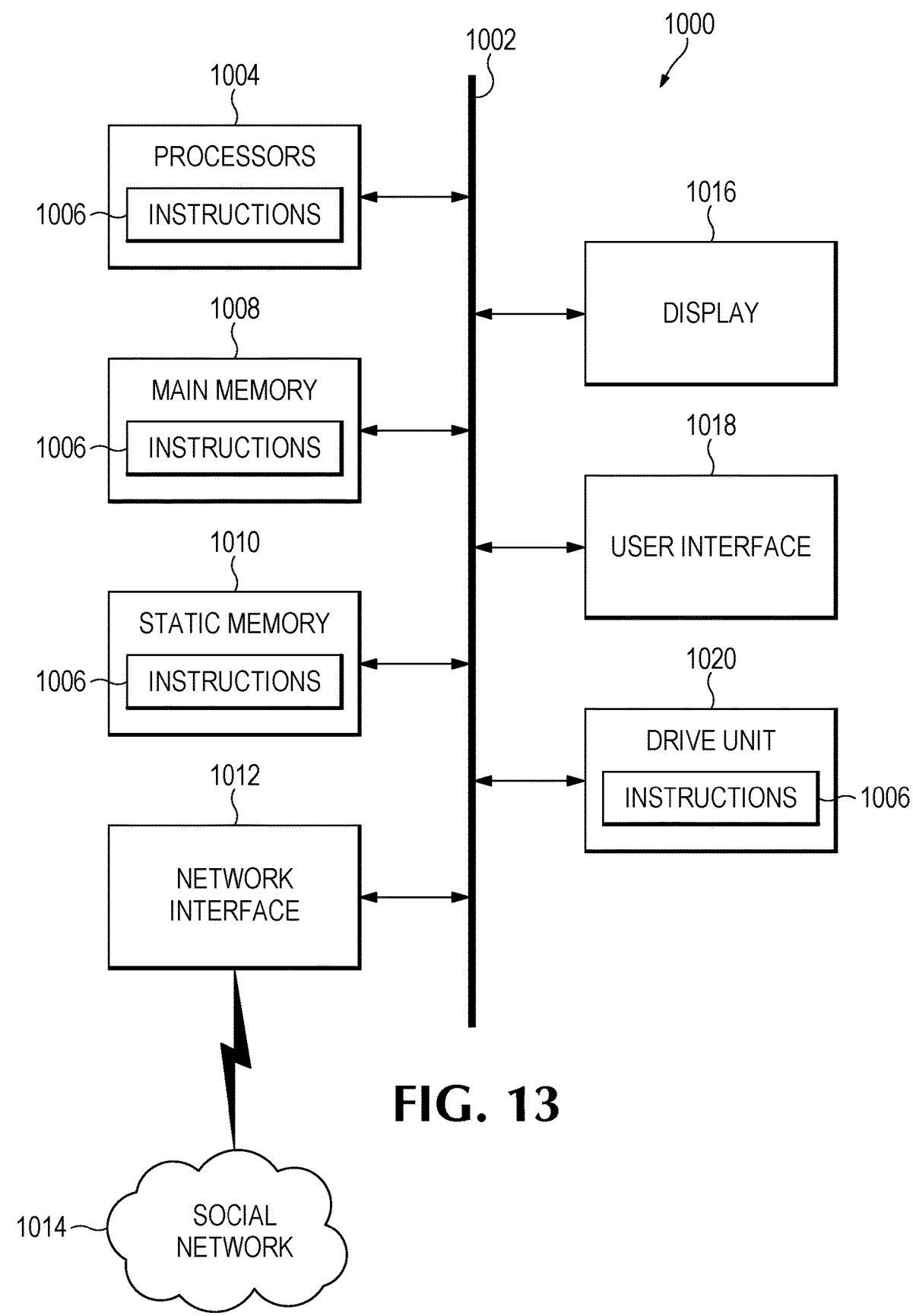
FIG. 13 shows a computer system used for controlling the ultrasonic transducer navigation system.

FIG. 13 shows a computing device 1000 used with the transducer navigation systems and performs any combination of processes discussed above. The computing device 1000 may operate in the capacity of a server or a client machine in a server-client network environment, or as a peer machine in a peer-to-peer (or distributed) network environment. In other examples, computing device 1000 may be a personal computer (PC), a tablet, a Personal Digital Assistant (PDA), a cellular telephone, a smart phone, a web appliance, or any other machine or device capable of executing instructions 1006 (sequential or otherwise) that specify actions to be taken by that machine.

While only a single computing device 1000 is shown, the computing device 1000 may include any collection of devices or circuitry that individually or jointly execute a set (or multiple sets) of instructions to perform any one or more of the operations discussed above. Computing device 1000 may be part of an integrated control system or system manager, or may be provided as a portable electronic device configured to interface with a networked system either locally or remotely via wireless transmission.

Processors 1004 may comprise a central processing unit (CPU), a graphics processing unit (GPU), programmable logic devices, dedicated processor systems, micro controllers, or microprocessors that may perform some or all of the operations described above. Processors 1004 may also include, but may not be limited to, an analog processor, a digital processor, a microprocessor, multi-core processor, processor array, network processor, etc.

Some of the operations described above may be implemented in software and other operations may be implemented in hardware. One or more of the operations, processes, or methods described herein may be performed by an apparatus, device, or system similar to those as described herein and with reference to the illustrated figures.

Processors 1004 may execute instructions or "code" 1006 stored in any one of memories 1008, 1010, or 1020. The memories may store data as well. Instructions 1006 and data can also be transmitted or received over a network 1014 via a network interface device 1012 utilizing any one of a number of well-known transfer protocols.

Memories 1008, 1010, and 1020 may be integrated together with processing device 1000, for example RAM or FLASH memory disposed within an integrated circuit microprocessor or the like. In other examples, the memory may comprise an independent device, such as an external disk drive, storage array, or any other storage devices used in database systems. The memory and processing devices may be operatively coupled together, or in communication with each other, for example by an I/O port, network connection, etc. such that the processing device may read a file stored on the memory.

Some memory may be "read only" by design (ROM) by virtue of permission settings, or not. Other examples of memory may include, but may be not limited to, WORM, EPROM, EEPROM, FLASH, etc. which may be implemented in solid state semiconductor devices. Other memories may comprise moving parts, such a conventional rotating disk drive. All such memories may be "machine-readable" in that they may be readable by a processing device.

"Computer-readable storage medium" (or alternatively, "machine-readable storage medium") may include all of the foregoing types of memory, as well as new technologies that may arise in the future, as long as they may be capable of storing digital information in the nature of a computer program or other data, at least temporarily, in such a manner that the stored information may be "read" by an appropriate processing device. The term "computer-readable" may not be limited to the historical usage of "computer" to imply a complete mainframe, mini-computer, desktop, wireless device, or even a laptop computer. Rather, "computer-readable" may comprise storage medium that may be readable by a processor, processing device, or any computing system. Such media may be any available media that may be locally and/or remotely accessible by a computer or processor, and may include volatile and non-volatile media, and removable and non-removable media.

Computing device 1000 can further include a video display 1016, such as a liquid crystal display (LCD) or a cathode ray tube (CRT) and a user interface 1018, such as a keyboard, mouse, touch screen, etc. All of the components of computing device 1000 may be connected together via a bus 1002 and/or network.

The system described above can use dedicated processor systems, micro controllers, programmable logic devices, or microprocessors that perform some or all of the operations. Some of the operations described above may be implemented in software, such as computer readable instructions contained on a storage media, or the same or other operations may be implemented in hardware.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or features of the flexible interface can be implemented by themselves, or in combination with other operations in either hardware or software.

References above have been made in detail to preferred embodiment. Examples of the preferred embodiments were illustrated in the referenced drawings. While preferred embodiments where described, it should be understood that this is not intended to limit the invention to one preferred embodiment. To the contrary, it is intended to cover alternatives, modifications, and equivalents as may be included within the spirit and scope of the invention as defined by the appended claims.

Having described and illustrated the principles of the invention in a preferred embodiment thereof, it should be apparent that the invention may be modified in arrangement and detail without departing from such principles. Claim is made to all modifications and variation coming within the spirit and scope of the following claims.

The invention claimed is:

1. A method comprising:
  attaching an ultrasonic transducer to a head of a patient;
  operating the ultrasonic transducer to apply an ultrasonic beam that is focused at a target area of a brain, wherein the ultrasonic beam includes a plurality of pulse trains, the pulse trains each including multiple individual pulses wherein the pulse trains are repeated at a rate between 1-4 Hertz, and the individual pulses have a maximum duration of 0.2-5 milliseconds with a maximum 10 milliseconds time period between the individual pulses of a respective pulse train.

2. The method of claim 1, wherein the target area of the brain corresponds to a hippocampus or an area of a temporal lobe that is associated with language functions.

3. The method of claim 1, wherein the ultrasonic beam is applied for 30-90 minutes.

4. The method of claim 1, wherein the target area has a width of 2.5-3.5 centimeters.

5. The method of claim 1, further wherein the ultrasonic beam is applied to the target area at a power level of 650-10,000 milliwatts (mW) per square centimeter ($Cm^2$).

6. One or more non-transitory computer-readable media (NTCRM) having instructions, stored thereon, that when executed by one or more processors, cause an ultrasonic transducer to:
  generate a focused ultrasonic beam; and
  direct the focused ultrasonic beam at a target area of a brain of a patient, wherein the ultrasonic beam includes a plurality of pulse trains, wherein the pulse trains each include multiple individual pulses, and wherein the pulse trains are repeated at a rate between 1-4 Hertz, and the individual pulses have a maximum duration of 0.2-5 milliseconds with a maximum 10 milliseconds time period between the individual pulses of a respective pulse train.

7. The one or more NTCRM of claim 6, wherein the target area of the brain corresponds to a hippocampus or an area of a temporal lobe that is associated with language functions.

* * * * *